(12) United States Patent
Eaton

(10) Patent No.: US 7,485,457 B2
(45) Date of Patent: Feb. 3, 2009

(54) ISOLATED/CLONED HUMAN NT2 CELL LINES EXPRESSING SEROTONIN AND GABA

(75) Inventor: Mary J. Eaton, Miami Beach, FL (US)

(73) Assignees: United States of America Department of Veterans Affairs, Washington, DC (US); University of Miami, Coral Gables, FL (US)

( * ) Notice: Subject to any disclaimer, the term of this patent is extended or adjusted under 35 U.S.C. 154(b) by 205 days.

(21) Appl. No.: 10/553,291

(22) PCT Filed: Jul. 17, 2003

(86) PCT No.: PCT/US03/19559

§ 371 (c)(1),
(2), (4) Date: Oct. 14, 2005

(87) PCT Pub. No.: WO2004/098621

PCT Pub. Date: Nov. 18, 2004

(65) Prior Publication Data

US 2006/0228338 A1  Oct. 12, 2006

Related U.S. Application Data

(60) Provisional application No. 60/463,315, filed on Apr. 17, 2003.

(51) Int. Cl.
*C12N 5/08* (2006.01)
*C12N 5/00* (2006.01)

(52) U.S. Cl. .................. 435/325; 435/365; 435/368; 424/93.1

(58) Field of Classification Search .............. None
See application file for complete search history.

(56) References Cited

U.S. PATENT DOCUMENTS

| | | | |
|---|---|---|---|
| 4,753,635 A | 6/1988 | Sagen et al. | |
| 4,980,174 A | 12/1990 | Sagen et al. | |
| 5,082,670 A | 1/1992 | Gage et al. | |
| 5,175,103 A | 12/1992 | Lee et al. | |
| 5,449,609 A * | 9/1995 | Younkin et al. | 435/7.21 |
| 5,629,159 A | 5/1997 | Anderson | |
| 5,656,267 A | 8/1997 | Sagen et al. | |
| 5,730,974 A | 3/1998 | Sagen | |
| 5,762,925 A | 6/1998 | Sagen | |
| 5,792,900 A | 8/1998 | Lee et al. | |
| 5,935,606 A | 8/1999 | Sagen | |
| 6,162,428 A | 12/2000 | Snable | |
| 6,214,334 B1 | 4/2001 | Lee et al. | |
| 6,254,865 B1 | 7/2001 | Freed et al. | |
| 6,358,739 B1 | 3/2002 | Baetge et al. | |

OTHER PUBLICATIONS

Lindvall et al., Nature Medicine 10, S42-S50 (2004).*
Isacson (Lancet Neurology 2003; 2: 417-224).*
Gernert et al., Experimental Neurology, vol. 176, Issue 1, Jul. 2002, pp. 183-192.*
Carlson et al., Neuroscience 119 (Jul. 16, 2003) 927-932.*
Berg-Johnsen J, Roste G, Solgaard T, Lundar T. Continuous intrathecal infusion of baclofen. A new therapeutic method for spasticity. Tidsskr Nor Laegeforen 1998;118: 3256-3260.
Kuraishi Y, Hirota N, Satoh M, Takagi H. Antinociceptive effects of intrathecal opioids, noradrenaline and serotonin in rats: mechanical and thermal algesic tests. Brain Res 1985;326: 168-171.
Fakhoury T, Abou-Khalil B, Blumenkopf B. EEG changes in intrathecal baclofen overdose: a case report and review of the literature. Electroencephalogr Clin Neurophysiol 1998;107: 339-342.
Postma TJ, Oenema D, Terpstra S, Bouma J. Cost analysis of the treatment of severe spinal spasticity with a continuous intrathecal baclofen infusion system. Pharmacoeconomics 1999;15: 395-404.
Zed PJ, Stiver HG, Devonshire V, Jewesson PJ. Coninuous intrathecal pump infusion of baclofen with antibiotic drugs for treatment of pump-associated meningitis. Case report. J Neurosurg 2000;92: 347-349.
Gock SB, Wong SH, Stormo KA, Jentzen JM. Self-intoxication with morphine obtained from an infusion pump. J Anal Toxicol 1999;23: 130-133.
Sauter K, Kaufman H, Bloomfield S, Cline S. Treatment of high-dose intrathecal morphine overdose. case report. J Neurosurg 1994;81: 143-146.
Wu CL and Patt RB. Accidental overdose of systemic morphine during intended refill on intrathecal infusion device. Anesth Analges 1992;75: 130-132.
Winnie AP, Pappas GD, DasGupta TK, Wang H. Subarachnoid adrenal medullary transplants for terminal cancer pain. Anesthesiology 1993;79: 644-653.
Wu HH, Wilcox GL, McLoon SC. Implantation of AtT-20 or genetically modified AtT-20/hENK cells in mouse spinal cord induced antinociception and opioid tolerance. J Neurosci 1994;14: 4806-4814.
Eaton MJ, Dancausse HR, Santiago DI, Whittemore SR. Lumbar transplants of immortalized serotonergic neurons alleviates chronic neuropathic pain. Pain 1997;72: 59-69.
Eaton MJ, Plunkett JA, Martinez MA, Lopez T. Transplants of neuronal cells bio-engineered to synthesize GABA alleviate chronic neuropathic pain. Cell Transplant 1999;8: 87-101.
Cejas PJ, Martinez M, Karmally S, McKillop M. Lumbar transplant of neurons genetically modified to secrete brain-derived neurotrophic factor attenuate allodynia and hyperalgesia after sciatic nerve constriction. Pain 2000;86: 195-210.
Eaton MJ and Whittemore SR. Autocrine BDNF secretion enhances the survival and serotonergic differentiation of raphe neuronal precursor cells grafted into the adult rat CNS. Exp Neurol 1996;140: 105-114.

(Continued)

*Primary Examiner*—David S Romeo
*Assistant Examiner*—Daniel C Gamett
(74) *Attorney, Agent, or Firm*—Dinesh Agarwal, P.C.

(57) ABSTRACT

Human cells isolated and/or cloned from human NT2 cells for expressing serotonin (5HT) and gamma-aminobutyric acid (GABA) are disclosed. These cells can be used as cellular minipumps to release serotonin and/or GABA to treat various neurological diseases, conditions, or disorders, particularly neurodegenerative disorders and the consequences of brain and spinal cord injuries (pain/spasticity).

2 Claims, 27 Drawing Sheets

OTHER PUBLICATIONS

Andrews PW, Damjanov I, Simon D, Banting GS. Pluripotent embryonal carcinoma clones derived from human teratocarcinoma cell line Tera-2. Lab Invest 1984;50: 147-162.

Pleasure SJ, Page C, Lee VMY. Pure, postmitotic, polarized human neurons derived from NTera 2 cells provide a system for expressing exogenous proteins in terminally differentiated neurons. J Neurosci 1992;12: 1802-1815.

Borlongan CV, Tajima Y, Trojanowski JQ, Lee VMY. Transplantation of cryopreserved human embryonal carcinoma-derived (NT2N cells) promotes functional recovery in ischemic rats. Ex Neurol 1998;149: 310-321.

Trojanowski JQ, Kleppner SR, Hartley RS, Miyazono M. Transfectable and transplantable postmitotic human neurons: potential "platform" for gene therapy of nervous system diseases. Exp Neurol 1997;144: 92-97.

Kondziolka D, Wechsler L, Goldstein S, Meltzer C. Transplantation of cultured human neuronal cells for patients with stroke. Neurology 2000;55: 565-569.

Nelson PT, Kondziolka D, Wechsler L, Goldstein S. Clonal human (hNT) neuron grafts for stroke therapy: neuropathology in a patient 27 months after implantation. Am J Pathol 2002;160: 1201-1206.

Eaton MJ, Frydel B, Lopez T, Nie X. Generation and initial characterization of conditionally immortalized chromaffin cells. J Cell Biochem 1999;79: 38-57.

Cheung WMW, Fu WY, Hui WS, Ip NY. Production of human CNS neurons from embryonal carcinoma cells using a cell aggregation method. BioTechniques 1999;26: 946-954.

Sarnat HB, Nochlin D, Born DE. Neuronal nuclear antigen (NeuN): a marker of neuronal maturation in early human fetal nervous system. Brain Dev 1998;20: 88-94.

Daadi MM, Saporta S, Willing AE, Zigova T. In vitro induction and in vivo expression of bcl-2 in the hNT neurons. Brain Res Bull 2001;56: 147-152.

Eaton MJ, Staley JK, Globus MYT, Whittemore SR. Developmental regulation of early serotonergic neuronal differentiation: the role of brain-derived neurotrophic factor and membrane depolarization. Dev Biol 1995;170: 169-182.

Bennett DJ, Gorassini M, Fouad K, Sanelli L. Spasticity in rats with sacral spinal cord injury. J Neurotrauma 1999;16: 69-84.

Siddall PJ, Yerzierski RP, Loeser J. Pain following spinal cord injury: clinical features, prevalence, and taxonomy. IASP Newsletter 2000;3: 3-7 (13 pages).

Hargreaves K, Dubner R, Brown F, Flores C. A new and sensitive method for measuring thermal nociception in cutaneous hyperalgesia. Pain 1988;32: 77-88.

Yezierski RP, Liu S, Ruenes GL, Kajander KJ. Excitotoxic spinal cord injury: behavioral and morphological characteristics of a central pain model. Pain 1998;75: 141-155.

Abraham KE, McGinty JF, Brewer KL. The role of kainic acid/AMPA and metabotropic glutamate receptors in the regulation of opioid mRNA expression and the onset of pain-related behavior following excitotoxic spinal cord injury. Neurosci 2001;104: 863-874.

Abraham KE and Brewer KL. Expression of c-fos mRNA is increased and related to dynorphin mRNA expression following excitotoxic spinal cord injury in the rat. Neurosci Lett 2001;307: 187-191.

Plunkett JA, Yu CG, Easton JM, Bethea JR. Effects of interleukin-10 (IL-10) on pain behavior and gene expression following excitotoxic spinal cord injury in the rat. Exp Neurol 2001;168: 144-154.

Abraham KE, McGinty JF, Brewer KL. Spinal and supraspinal changes in opioid mRNA expression are related to the onset of pain behaviors following spinal cord injury. Pain 2001;90: 181-190.

Abraham KE, Brewer KL, McGinty JF. Opioid peptide messenger RNA expression is increased at spinal and supraspinal levels following excitotoxic spinal cord injury. Neurosci 2000;99: 189-197.

Morrow TJ, Paulson PE, Brewer KL, Yezierski RP. Chronic, selective forebrain responses to excitotoxic dorsal horn injury. Exp Neurol 2000;161: 220-226.

Brewer KL and Yezierski RP. Effects of adrenal medullary transplants on pain-related behaviors following excitotoxic spinal cord injury. Pain 1998;798: 83-92.

Schwartz ED, Yezierski RP, Pattany PM, Quencer RM, Diffusion-weighted MR imaging in a rat model of syringomyelia after excitotoxic spinal cord injury. Am J Neuroradiol 1999;20: 1422-1428.

Yezierski RP, Santana M, Park SH, Madsen PW. Neuronal degeneration and spinal cavitation following intraspinal injections of quisqualic acid in the rat. J Neurotrauma 1993;10: 445-456.

Widerstrom-Noga EG, Felipe-Cuervo E, Broton JG, Duncan RC. Perceived difficulty in dealing with consequences of spinal cord injury. Arch Phys Med Rehabil 1999;80: 580-586.

Yezierski RP. Pain following spinal cord injury: the clinical problem and experimental studies. Pain 1996;68: 185-194.

Bennett GJ and Xie Y-K. A peripheral mononeuropathy in rat that produces disorders of pain sensation like those seen in man. Pain 1988;33: 87-107.

Kim SH and Chung JM. An experimental model for peripheral neuropathy produced by segmental spinal nerve ligation in the rat. Pain 1992;50: 355-363.

Yezierski RP, Liu S, Ruenes GL, Kajander KJ. Behavioral and pathological characteristics of a central pain model following spinal injury. VIIIth World Congress on Pain 1996; IASP Press, p. 379.

Yezierski RP and Park SH. The mechanosensitivity of spinal sensory neurons following intraspinal injections of quisqualic acid in the rat. Neurosci Lett 1998;157: 115-119.

Smart D, Hirst RA, Hirota K, Grandy DK, Lambert DG. The effects of recombinant rat mu-opioid receptor activation in CHO cells on phopholipase C, [Ca2+]i and adenyl cyclase. Br J Pharmacol 1997; 120: 1165-1171.

Schumm MA, Castellanos DA, Frydel BL, Sagen J. Direct cell-cell contact required for neurotrophic effect of chromaffin cells on neural progenitor cells. Brain Res., 146 (1-2):1-13.(2003).

Schumm MA, Castellanos DA, Frydel BR, Sagen J. Enhanced viability and neuronal differentiation of neural progenitors by chromaffin cell co-cultute. Brain Res., 137(2):115-25(2002).

Schumm MA, Castellanos DA, Frydel BR, Sagen J. Improved neural progenitor cell survival when cografted with chromaffin cells in the rat striatum. Exp Neurol., 185(1):133-42 (2004).

Hama AT, Siegan JB, Herzberg U, Sagen J. 1. NMDA-induced spinal hypersensitivity is reduced by naturally derived peptide analog [Ser1]histogranin. Pharmacol Biochem Behav. 62(1):67-74 (1999).

Siegan JB, Hama AT, Sagen J. Suppression of neuropathic pain by a naturally-derived peptide with NMDA antagonist activity. Brain Res., 755(2):331-4 (1997).

Siegan JB, Sagen J. A natural peptide with NMDA inhibitory activity reduces tonic pain in the formalin model. Neuroreport., 8(6):1379-81 (1997).

Eaton MJ, Herman JP, Jullien N, Lopez TL, Martinez M, Huang J. Immortalized chromaffin cells disimmortalized with Cre/lox site-directed recombination for use in cell therapy for pain after partial nerve injury. Exp Neurol. 175(1):49-60 (2002).

Eaton MJ, Martinez M, Karmally S, Lopez T, Sagen J. Initial characterization of the transplant of immortalized chromaffin cells for the attenuation of chronic neuropathic pain. Cell Transplant., 9(5):637-56 (2000).

NasiriNezhad F, Sagen J. NMDA antagonist peptide supplementation enhances pain alleviation by adrenal medullary transplants. Cell Transplant., 14(4):203-11 (2005).

Hama A, Sagen J. Selective antihyperalgesic effect of [Ser$^1$] histogram on complete Freund's adjuvant-induced hyperalgesia in rats. PAIN 95:15-21 (2002).

Reynolds, G.P. et al. (1999), Brain Neurotransmitter Deficits in Mice Transgenic for the Huntington's Disease Mutation, J. Neurochem. vol. 72, p. 1773-1776, especially p. 1774 and Table 1.

Guillemain I., Alonso G., Patey G., Privat A. and Chaudieu I. Human NT2 Neurons Express a Large Variety of Neurotransmission Phenotypes In Vitro. The Journal of Comparative Neurology 422:380-395 (2000).

Eaton M.J. Wolfe S.Q., Martinez M., Hernandez C.F., Huang J., Frydel B.R., and Gomez-Marin O. Subarachnoid Transplant of a Human Neuronal Cell Line Attenuates Chronic Allodynia and Hyperalgesia After Excitotoxic Spinal Cord Injury in the Rat. The Journal of Pain, vol. 8, No. 1 (Jan.), 2007:pp. 33-50.

Wolfe S.Q., Garg M., Cumbebatch N.M.A., Furst C., Martinez M., Hernandez M., Reimers R., Berrocal Y., Gomez-Marin O., and Eaton M.J. Optimizing the transplant dose of a human neuronal cell line graft to treat SCI pain in the rat. Neuroscience Letters 414 (2007) 121-125.

Pleasure S.J., and Lee V.M.Y. NTera 2 Cells: A Human Cell Line Which Displays Characteristics Expected of a Human Committed Neuronal Progenitor Cell, Journal of Neuroscience Research 35:585-602 (1993).

Wechsler, L.R. and Kondziolka, D. Cell Therapy: Replacement. *Stroke* 2003;34;2081-2082.

Howells D. Stem Cells: Do They Replace or Stimulate?. Stroke. 2003;34:2082-2083.

International Search Report and Written Opinion dated Feb. 19, 2008, in International Application No. PCT/US05/38233 (6 pp.).

Abou-Donia, M.M., Wilson, S.P., Zimmerman, T.P., Nichol, C.A., Viveros, O.H. Regulation of guanosine triphosphate cyclohydrolase and tetrahydrobiopterin levels and the role of the cofactor in tyrosine hydroxylation in primary cultures of adrenomedullary chromaffin cells. J Neurochem, 46, 1190-1199 (1986).

Aunis, D., Hesketh, J., Devilliers, G. Immunohistochemical and immunocytochemical localization of myosin, chromogranin A and dopamine-β-hydroxylase in nerve cells in culture and adrenal glands. J Neurocytol, 9, 255-274 (1980).

Bachoud-Levi, A.C., Remy, P., Nguyen, J.P., Brugieres, P., Lefaucheur, J.P., Bourdet, C., Baudic, S., Gaura, V., Maison, P., Peschanski, M. Motor and cognitive improvements in patients with Huntington's disease after neural transplantation. Lancet, 356, 1975-1979 (2000).

Cahill, A.L., Eertmoed, L., Mangoura, D., Perlman, R. Differential regulation of phenylethanolamine-N-methyltransferase expression in two distinct subpopulations of bovine chromaffin cells. J. Neurochem., 67, 1217-1224 (1996).

Cairns L, Crotta S, Minuzzo M, Ricciardi-Castagnoli P, Pozzi L, Ottolenghi S: Immortalization of neuro-endocrine cells from adrenal tumors arising in SV40 T-transgenic mice. Oncogene 14:3093-3098 (1997).

Czech KA, Sagen J: Update on cellular transplantation into the CNS as a novel therapy for chronic pain. Prog.Neurobiol. 46:507-529 (1995).

Duplan H, Bes JC, Tafani M, Sallerin B, Sagen J, Ohayon E, Lazorthes Y, Tkaczuk J: Adrenal medullary explants as an efficient tool for pain control: adhesive biomolecular components are involved in graft function ex vivo. Exp Neurol, 163:331-347(2000).

Eaton, M.J., Blits, B., Ruitenberg, M.J., Verhaagen J., Oudega, M. Amelioration of chronic neurpathic pain by adeno-associated viral (AAV) vector-mediated overexpression of BDNF in the rat spinal cord. Gene Ther, 9, 1387-1395 (2002a).

Eaton MJ: Emerging cell and molecular strategies for the study and treatment of painful peripheral neuropathies. J Peripher Nerv Sys 5:59-74 (2000).

Eaton, M.J., Gudehithlu, K.P., Quach, T., Silvia, C.P., Hadjiconstantinou, M., Neff, N.H. Distribution of aromatic L-amino acid decarboxylase mRNA in mouse brain by in situ hybridization histology. J. Comp. Neurol., 337, 640-654 (1993).

Eaton, M.J., Herman, J.P., Jullien, N., Lopez, T., Martinez, M., Huang, J. Immortalized chromaffin cells disimmortalized with Cre/lox site-directed recombination for use in cell therapy for pain. Exp Neurol, 175, 49-60 (2002b).

Giger, R.J., Wolfer, D.P., De Wit, G.M., Verhaagen, J. Anatomy of rat semaphorin III/collapsin-1 mRNA expression and relationship to developing nerve tracts during neuroembryogenesis. J Comp Nerol, 375, 378-392 (1996).

Lazorthes Y, Sagen J, Sallerin B, Tkaczuk J, Duplan H, Sol JC, Tafani M, Bes JC: Human chromaffin cell graft into the CSF for cancer pain management: a prospective phase II clinical study. Pain 87:19-32 (2000).

Muench, M.O., Ratcliffe, J.V., Nakanishi, M., Ishimoto, H., Jaffe, R.B. Isolation of definitive zone and chromaffin cells based upon expression of CD56 (neural cell adhesion molecule) in the human fetal adrenal gland. J Clin Endocrinol Metab, 88, 3921-3930 (2003).

Paillard F: reversible cell immortalization with the cre-lox system. Hum.Gene Ther. 10:1597-1598 (1999).

Pal, R., Eaton, M.J., Islam, S., Hake-Frendscho, M., Kumar, K.N., Michaelis, E.K. Immunocytochemical and in situ hybridization studies of the expression and distributional of three subunits of a complex with N-methyl-D-aspartate receptor-like properties. Neurosci., 94, 1291-1311 (1999).

Pasterkamp, R.J., Giger, R.J., Ruitenberg, M.J., Holtmaat, A., De Wit, J., de Winter, F., Verhaagen, J. Expression of the gene encoding the chemorepellent semaphorin III is induced in the fibroblast component of neural scar tissue formed following injuries of adult but not neonatal CNS. Mol Cell Neurosci, 13, 143-166 (1999).

Pear, W.S. III Transduction of genes using retrovirus vectors. In: Ausabel, F.M., Brent, R., Kingston, R.E., Moore, D.D., Seigman, J.G., Smith, J.A. & Struhl, K. (eds),. Current protocols in molecular biology. John Wiley and Sons, New York (1995).

Pear, W.S., Nolan, G.P., Scott, M.L., Baltimore, D. Production of high-titer helper-free retroviruses by transient transfection. Proc. Nat. Acad. Sci., U. S. A., 90, 8392-8396 (1993).

Unsicker, K. & Muller, T.H. Purification of bovine adrenal chromaffin cells by differential plating. J. Neurosci. Meth., 4, 227-241 (1981).

Wang H, Sagen J: Attenuation of pain-related hyperventilation in adjuvant arthritic rats with adrenal medullary transplants in the spinal subarachnoid space. Pain 63:313-3201 (1995).

Duplan et al, Generation of conditionally immortalized cell lines genetically modified to over-express opioid peptides for chronic pain control, (Abstract) Exp Neurol, 175 (2): 433 (2002).

Wang X-T, Eaton MJ. Sagen J. Generation of conditionally immortalized serotonergic pineal cells for transplantation in chronic pain. Soc Neurosci, Abstract 23: 1455 (1997).

Kim P, Seasholtz AF, Sagen J. Generation of opioid-producing PC12 cells for transplantation in chronic pain. Amer Soc Neural Transpl, Abstract 3:34 (1996).

Kim PH, Wang X-T, Seasholtz A, Sagen J, Unnerstall JR. A met-enkephalin producing PC12 cell line as an alternative donor source for neural transplants in the reduction of chronic pain. Soc Neurosci, Abstract 22: 1021 (1996).

Eaton MJ, Frydel B, Lopez T, Nie XT, Huang J, McKillop J, Sagen J. Generation and initial characterization of conditionally immortalized chromaffin cells. J Cell Biochem., 79(1):38-57 (2000).

* cited by examiner

2 wk, phase

2 wk, 5HT

2 wk, 5HT

2 wk, GABA

2 wk, NeuN

2 wk, DAPI

2 wk, NuMA hNT2.19, NuMA hNT2.17, DAPI hNT2.17, NuMA

ISOLATED/CLONED HUMAN NT2 CELL LINES EXPRESSING SEROTONIN AND GABA

CROSS-REFERENCE TO RELATED APPLICATIONS

The present application claims priority on prior U.S. Provisional Application Ser. No. 60/463,315, filed Apr. 17, 2003, and which is incorporated herein in its entirety by reference.

STATEMENT REGARDING FEDERALLY SPONSORED RESEARCH OR DEVELOPMENT

The work leading to the present invention was supported by one or more grants from the U.S. Government. The U.S. Government therefore has certain rights in the invention.

BACKGROUND OF THE INVENTION

The present invention is directed to the creation of two novel cell lines, the GABAergic hNT2.17 and serotonergic hNT2.19, synthesizing and releasing the neurotransmitters GABA and serotonin (5HT), both derived from the human NT2 cell line, and which are useful for the treatment of pain and spasticity and other traumatic or neurodegenerative injuries to the nervous system. These cells are stably transplanted into host rodent animals in models of pain and spasticity.

Chronic pain and spasticity constitute some of the significant problems following spinal cord injuries (SCI), interfering with rehabilitation and daily activities, which in turn leads to significant complications in these patients. However, there are no effective, completely safe therapies for the reduction of these conditions (and other related to neural trauma and degeneration).

Oral baclofen, the GABA-B receptor agonist, has often been the drug of choice for spasticity (Reference 1) due to spinal cord trauma, and baclofen and opioids have been used for the relief of chronic pain (Reference 2). However, oral baclofen is often ineffective at non-toxic doses, because large doses are required to cross the blood-brain barrier and can lead to subsequent CNS effects (Reference 3), usually not well tolerated by spastic patients. Intrathecally administered baclofen is currently FDA-approved for those patients with spinal cord injury who are refractory or can not tolerate oral baclofen, but spinally-delivered baclofen via programmable implantable electronic pumps is also fraught with problems, such as high costs, catheter twisting, infection at the implant site, overdosing and the development of tolerance with increasing doses of baclofen required for relief (References 4 and 5). Furthermore, the efficacy of baclofen pumps is mainly in terms of lower extremity spasticity and the treatment has little effect on upper extremity spasticity. Intrathecal morphine has been used via electronic pump and has been prescribed for use in neuropathic pain, but often has complications of tolerance, overdose, and problems related to the pump itself (References 6-8).

Transplants of primary cultured cells near the dorsal horn of the spinal cord that release peptides and neurotransmitters have offered a new direction in the treatment of chronic pain (Reference 9). However, primary cells are difficult to obtain, non-homogeneous, and would require that each batch be tested before clinical use. Transplantation of immortalized cell lines genetically-modified to release neuroactive antinociceptive peptides (Reference 10), inhibitory neurotransmitters (References 11 and 12) and neurotrophins (Reference 13) in chronic pain, and to upregulate inhibitory neurotransmitter synthesis (Reference 14) offers a renewable source of cells that can act as cellular minipumps, are able to respond to the microenvironment of the cord, and should reduce or eliminate side effects associated with the large doses of pharmacologic agents required for centrally-acting pain-reducing agents. A naturally-immortalized human embryonal carcinoma cell line, NTera2cl.D/I (NT2), differentiates irreversibly into several morphologically and phenotypically distinct cell types, which include terminally differentiated postmitotoc CNS neurons (Reference 15). Successive re-plating of retinoic acid-treated NT2 cells, in the presence of growth inhibitors, results in the isolation of purified human neurons (Reference 16), that have been extensively characterized and tested in vivo in a number of animal models of traumatic injury and neurodegenerative disease (Reference 17). The potential application of NT2 neurons in cell transplantation therapy for CNS disorders, and their use as vehicles for delivering exogenous proteins into the human brain for gene therapy, has been recently demonstrated (Reference 18). Such NT2 neurons are being currently used in Phase-II clinical trials for the treatment of stroke, and have been approved by FDA for such trials (References 19 and 20). However, such NT2 cells contain a variety of neural phenotypes, and would provide a plethora of neuroactive substances if used for the specific treatment of problems such as pain or SCI-associated spasticity.

U.S. Pat. Nos. 5,082,670, 5,175,103, 5,792,900, 6,162,428, 6,214,334, and 6,254,865, are directed to the use of the parental human NT2 cell line for a variety of disorders, but none describe the creation or use of individual cell lines derived from the NT2 or NT2/D cell lines.

In order to ameliorate various neurological diseases, conditions, or disorders, the present invention creates two novel human neural cell lines, subcloned and derived from the human NT2 cell line, where each subcloned cell line synthesizes and secretes bioactive agents, such GABA or serotonin (5HT). Transplants of these secreting human neural cell lines are believed to reduce consequences of spinal trauma after transplant in or near the spinal cord.

OBJECTS AND SUMMARY OF THE INVENTION

The principal object of the present invention is to provide an isolated and/or cloned human cell and/or cell line which expresses a bioagent, such as serotonin (5HT) or gamma-aminobutyric acid (GABA).

Another object of the present invention is to provide an isolated and/or cloned human cell and/or cell line expressing serotonin (5HT) or gamma-aminobutyric acid (GABA) which can be used to treat a neurological disease, condition, or disorder, such as pain, spasticity, epilepsy, depression, mobility disorder, sensory disorder, Parkinson's, or Alzheimer's disease.

Yet another object of the present invention is to provide an isolated and/or cloned human cell and/or cell line expressing serotonin (5HT) or gamma-aminobutyric acid (GABA) that releases specific bioagents to reverse the damage to the nervous system, which can be safely used for transplant into or near the brain or spinal cord after injury or in disease states.

An additional object of the present invention is the use of clonal human hNT2 neuronal cell lines as cellular minipumps to release serotonin (5HT) and/or gamma-aminobutyric acid (GABA) to treat neurodegenerative disorders and consequences of brain and spinal cord injuries.

In summary, the main object of the present invention is to provide an isolated and/or cloned human cell and/or cell line that expresses serotonin (5HT) or gamma-aminobutyric acid (GABA). The cells can be used to treat various neurological diseases, conditions and/or disorders, such as pain, spasticity, epilepsy, depression, mobility disorder, sensory disorder, Parkinson's, and Alzheimer's, and/or to reverse the damage to the nervous system.

At least one of the above-noted objects is met, in part, by the present invention, which in one aspect includes a cell for expressing serotonin (5HT) isolated from a human NT2 cell line.

Another aspect of the present invention includes a cell for expressing gamma-aminobutyric acid (GABA) isolated from a human NT2 cell line.

Another aspect of the present invention includes a cell for expressing serotonin (5HT) cloned from a cell obtained from a human NT2 cell line.

Another aspect of the present invention includes a cell for expressing gamma-aminobutyric acid (GABA) cloned from a cell obtained from a human NT2 cell line.

Another aspect of the present invention includes treating a neurological disease, condition, or disorder by administering to a subject in need thereof a suitable amount of serotonin (5HT) expressing hNT2 cells.

Another aspect of the present invention includes treating a neurological disease, condition, or disorder by administering to a subject in need thereof a suitable amount of gamma-aminobutyric acid (GABA) expressing hNT2 cells.

Another aspect of the present invention includes a composition for treating a neurological disease, condition, or disorder, which includes a cell for expressing a bioagent selected from the group consisting of serotonin (5HT), and yaminobutyric acid (GABA), and a suitable carrier, wherein the cell is isolated from a human NT2 cell line.

Another aspect of the present invention includes a composition for treating a neurological disease, condition, or disorder, which includes a cell for expressing a bioagent selected from the group consisting of serotonin (5HT), and yaminobutyric acid (GABA), and a suitable carrier, wherein the cell is cloned from a cell obtained from a human NT2 cell line.

Another aspect of the present invention includes a method of producing a mammal useful for studying a neurological disease, condition, or disorder by transplanting a suitable amount of serotonin expressing human NT2 cells into or near a mammal's spinal cord, brain, or peripheral nervous system.

Another aspect of the present invention includes a method of producing a mammal useful for studying a neurological disease, condition, or disorder by transplanting a suitable amount of gamma-aminobutyric acid (GABA) expressing human NT2 cells into a mammal's spinal cord, brain, or peripheral nervous system.

Another aspect of the present invention includes a cell transplant material, which includes serotonin expressing human NT2 cells.

Another aspect of the present invention includes a cell transplant material, which includes gamma-aminobutyric acid (GABA) expressing human NT2 cells.

BRIEF DESCRIPTION OF THE DRAWINGS

The above and other objects, novel features and advantages of the present invention will become apparent from the following detailed description of the preferred embodiment(s) invention, as illustrated in the drawings, in which.

DETAILED DESCRIPTION OF THE PREFERRED EMBODIMENT(S) OF THE INVENTION

Figure 1A:
FIG. 1A is a phase-contrast photomicrograph of differentiated (one week) hNT2.19 cells.

The availability of an inexhaustible supply of human cells which can make specific biologic agents to reverse the damage to the nervous system that could be safely used for transplant into or near the brain or spinal cord after injury or in disease states would be very useful to treat a variety of problems such as pain, spasticity, epilepsy, immobility or related problems. Ideally such cell sources should not be derived from human embryos or cadavers, and should not form tumors if placed in the patient, but would still function and survive for long periods. Such cell transplants would not be required to replace missing cells, but would function as cellular minipumps, releasing beneficial molecules near damaged tissue so that some of the damaged tissue and hence, human function, could be repaired or improved.

The present invention is directed to deriving some of these clinically useful cells by isolating unique colonies of daughter cells from a naturally-immortal human neuronal cell line called hNT2, so that the daughter colonies are different from each other and the original parent hNT2 cell type, a process called subcloning. However, these new daughter cell lines retain the property of being naturally-immortal, when they are grown in the absence of retinoic acid (RA). Is this condition, they multiply indefinitely, allowing them to be frozen, stored, and restarted at any time in culture. If the cells are treated with RA for a few weeks, they become human neurons, no longer capable of division. Such cells can be safely transplanted into the potential patient, with no danger of tumor formation, since they become human neurons irreversibly, which no longer divide and multiply. In addition, since they are unique derivative cell lines, they have characteristic features, such as the ability to make and secrete useful agents, such as the neurotransmitters serotonin (5HT) and gamma-aminobutyric acid (GABA).

The ability of transplants of these unique hNT2 cell lines to relieve chronic pain and spasticity was tested in animal models after spinal cord injury (SCI), and it is expected that they would be beneficial for these conditions. Transplant of cell lines that secrete 5HT or GABA that could be used in the human conditions, such as the consequences of SCI where chronic pain and spasticity are important problems clinically, would make them a desirable new tool for the SCI population. However, such subcloned cell lines, derived from the parental hNT2 neuronal cell line have great potential for cell therapy for the treatment of a variety of traumatic and neurodegenerative diseases in humans. Examples of what these and other subcloned NT2 cell lines could make include GABA, 5HT, catecholamines, opioids, as well as many other peptides or agents unknown at this time.

The present invention is therefore directed to isolating novel and specific, well-characterized cell lines from the hNT2 parent line by conventional subcloning methods, and testing the use of individual novel NT2 cell lines for the treatment of traumatic consequences, such as pain and spasticity. However, such cell line transplants could also be used to treat a variety of neural trauma and neurodegenerative problems, including epilepsy, depression, mobility and sensory disorders, including Parkinson's and Alzheimer's disease.

The basis of the proposed efficacy of this invention is that release of neuroactive agents, such as GABA or 5HT, from such cell transplants will provide a low, local dose of agent in the area of neural substrate where needed, without a broad systemic effect, and such cells, since immortalized and grown in vitro can be well-characterized and tested for homogeneity and safety for human use.

Subcloning and Characterization of NT2 GABA and 5HT Neuronal Cell Lines

Conventional methods for serial dilution and subcloning with cloning rings are used to isolate proliferating and rapidly-growing colonies of the parental hNT2 cells, that form cell lines, in vitro (Reference 21). A more rapid cell-aggregation method (Reference 22) is used, described below, for the differentiation of proliferating NT2 cells that only requires 14 days of retinoic acid (RA) treatment, to characterize each clonal NT2 clonal line for a GABA or 5HT phenotype. Each clonal line is initially stained for GABA or 5HT production with immunohistochemical methods (Reference 12) using commercially-available antibodies directed against GABA or 5HT. GABA- or 5HT-containing NT2 cell lines are double-labeled with the neuronal marker, neuronal nuclear marker (NeuN) (Reference 23), or the human nuclear matrix antigen, NuMA (Reference 24) to insure the phenotype is both GABAergic or 5HTergic and neuronal. The content and release of the neurotransmitter GABA or 5HT from candidate GABA or 5HT NT2 cell lines is evaluated by standard high performance liquid chromatography (HPLC) methods, described below, and is used to characterize other neurotransmitter cell lines (References 12 and 25). Cell lines which synthesize and release greater than 100 pmole GABA or $5HT/10^6$ cells/min are used for further characterization and transplant experiments. Some of the NT2 neuronal cell lines which do not synthesize or secrete GABA or 5HT and do not stain positive for these agents by antibody methods, but survive well in vitro are used as the negative-control NT2 cell line for further transplant work in models of pain and spasticity after SCI.

Rapid Aggregation Method for Differentiation and Identification of NT2 Clones

This method was adapted from an earlier published aggregation method for NT2 cell cultures (Reference 22). Confluent proliferating NT2 cells, expanded in non-tissue culture 100 mm plates, are treated for two weeks with 10 micromolar all-trans retinoic acid (RA), in high-glucose DMEM media, made pH 8.0 with 15 mM HEPES buffer. Remaining cells are replated in poly-L-lysine/laminin-(PLS/lam)coated tissue culture plates (20 ug/ml), and the high-glucose DMEM supplemented with 2 mM Glutamine, pH 7.4. Twenty-four hours after replating, cytosine-D-arabinofuranoside (araC), 1 micromolar, and uridine, 10 micromolar, are added to the media for seven days. Differentiation is continued for one or two weeks after the removal of the mitogen inhibitors on PLS/lam-coated plastic slides. Individual clonal lines are examined for antibody staining and characterization for GABA or 5HT and NuMA or NeuN and other markers.

Immunohistochemistry Methods: In Vitro and In Vivo

Staining for GABA or 5HT in NT2 cell lines is done in a conventional manner (Reference 12). The specific GABA or 5HT signal are examined in both proliferating and differentiated cell lines, as well as in transplant grafts, in models of pain and spasticity. Any suspected GABA or 5HT cell lines are also examined for GABA or 5HT content and release by HPLC (below) to insure that any suspected GABA or 5HT synthesis and release from the cells is authentic.

Methods for NeuN staining have been previously published (Reference 23). The human-specific NuMA has been examined in parental hNT2 grafts in vivo (Reference 24). NeuN and NuMA are examined in differentiated clonal cultures to insure that clonal cell lines are human neurons. Typical methods for in vitro GABA, NeuN, and NuMA staining are as follows. Fix cells with Lana's (4% paraformaldehyde plus 10% picric acid, pH 7.4) at 4° C. for ten minutes. Rinse and permeabilize cells with 0.4% Triton X-100 in PBS. Incubate ten minutes at room temperature. Incubate with primary antibody for 12 hrs at 4° C. For serotonin (5HT): Rabbit antisera raised against 5HT (Immunostar), 1:1,000/PBS. For GABA: Guinea pig antisera raised against GABA (Protos Biotech Corp.), 1:250 PBS. For NeuN: Mouse anti-neuronal Nuclei monoclonal antibody (Chemicon) 1 mg/ml., 1:100 PBS. For NuMA: Monoclonal NuMA (Ab-2) (Oncogene) 100 ug/ml., 1:100 PBS. Rinse and incubate with secondary antibody for 2 hrs. Typical secondary antibodies include: For GABA: Alexa Fluor 488 Goat anti-guinea pig (Molecular Probes), 1:150 PBS. For NeuN and NuMA: Alexa fluor 488 Goat anti-mouse (Molecular Probes), 1:150 PBS. For brightfield images, ABC Elite kits (Vector), with VIP substrate, and appropriate secondary for each species of primary antibody are used.

HPLC GABA in NT2 Cell Lines

Either GABA content is measured in water-lysed cells, or GABA release is measured in buffer containing normal (2.95 mM) or high (100 mM) KCl incubated for 15 min with cultures of two-week differentiated cells. The HPLC system consists of a solvent-delivery pump (Waters 510 Pump), an autosampler (Waters 717 plus Autosampler) and an electrochemical detector (ESA Coulochem II; Electrode: ESA Model 5011 Analytic Cell; Guard Cell: Model 5020). Elution is carried out at room temperature with a reversed-phase column (3 uM, C18, 80×4.6, HR-80, ESA) and a mobile phase of 0.1 M Sodium Acetate (pH=5)-acetonitrile (73:27, v/v) at a flow rate of 0.6 ml/min. To an OPA solution (2 mg of o-Phthaldialdehyde (OPA) in 0.2 ml Methanol), 0.8 ml of 0.1 M Borax Buffer, pH 10.4 and 5 µl of 2-mercaptoethanol (2MCE) are added. 4 min before the injection on the column, to prepare the OPA reagent. The OPA reagent and sample are mixed (1:4) and incubated at room temperature in the autosampler before injection. After injection, the GABA peak appearance time is about 5 min in 27% Ace Mobile Phase. Determination of 5HT synthesis will follow similar published methods (Reference 25).

Animal Model of Spasticity

A sacral transection for the development of spasticity has been developed in a rat model (Reference 26). Complete sacral (S2) spinal transection only affected the tail musculature, and otherwise was minimally disruptive to normal functions, not interferring with bowel, bladder, or hindlimb locomotor function. After spinal transection, initially the tail musculature was paralyzed for two weeks, followed by increasing hypertonia, hyperreflexia, and clonus that developed over weeks and remains permanent in tail function, easily assessed in the awake rat. Muscle stretch or cutaneous stimulation of the tail produced muscle spasms and marked increases in muscle tone, measured with force or EMG recordings (Reference 26). Spontaneous or reflex induced flexor and extensor spasms are readily seen in the unconstrained tail. The tail and areas surrounding the tail, including the skin and hair develop thermal hyperalgesia and tactile allodynia, suggesting a variety of sensory disturbances, including the development of chronic pain, features that often accompany spasticity at- or below-level spinal injury in humans (Reference 27). These characteristic motor (and sensory) responses develop during 4 distinct time periods (stage 1-4, acute through chronic, day 1 to >60 days) and surgical rats are compared to uninjured animals. The following rating system is used to evaluate animals: 0, minimal activity (flacid); +, normal activity; ++, increased activity; and, +++, maximal activity. To test for thermal hyperalgesia, a tail-flick test is used (Reference 28), with an automated Hargreaves device to determine the latency of response to the noxious thermal stimulus. All spasticity and pain behaviors are examined before and after surgeries until at least 60 days after S2 spinal lesion, with cell transplants placed two weeks after SCI.

Animal Model of Excitotoxic SCI and Chronic Pain

A recently developed model of excitotoxic SCI (Reference 29) is now being used by many groups to study the mechanisms and behaviors associated with chronic pain and spinal injury (References 30-36). This model not only allows for quantitative assessment of behavioral hypersensitivity after injury but, with focused spinal microinjections of the excitotoxic agent, also permits an investigation of the cellular mechanisms in the cord that might be associated with the onset of that pain. As well, this excitotoxic SCI pain model has been used to evaluate the effects of cell transplantation of primary adrenal chromaffin tissue to reverse the chronic behavioral allodynia and hyperalgesia (Reference 36) that chemical lesioning of the dorsal horn pain processing centers produces. The model makes use of intraspinal injection of the glutamate receptor agonist, quisqualic acid (QUIS) just above the lumbar segments which control sensory function in the hindlimbs, which leads to predictable and quantifiable temporal profile of pain behaviors, without the complications of a loss in motor systems, paralysis, or loss of bowel and bladder function (Reference 29).

Intraspinal injection of quisqualic acid (QUIS) produces injury with pathological characteristics similar to those associated with ischemic and traumatic SCI (References 35 and 37). The pathological changes after QUIS include neuronal loss, demyelination, cavitation, glial responses, perivascular changes, breakdown of blood-brain barrier and inflammation (Reference 38). In addition, significant, evoked mechanical allodynia and thermal hyperalgesia have been shown to be important components. Each of these behaviors is indicative of altered sensory function and/or pain, similar to that reported after SCI (Reference 39). After spinal transplantation of primary adrenal tissue following QUIS injections, pain related behaviors, including the progression of spontaneous excessive grooming behavior and hypersensitivity to mechanical stimuli were significantly reduced (Reference 36). These transplantation results in a pain-related model of SCI suggests that similar human cell transplants might be a meaningful therapeutic strategy for the large proportion of SCI patients that report intractable chronic pain after SCI (Reference 40).

Allodynia is the response, measured as a change in threshold, to a normally non-painful stimuli, such as cold (0-4° C.) or tactile stimulation. Hyperalgesia is the response measured as a change in threshold to a painful stimuli, such as heat or pressure. The thermal hyperalgesia response to heat using an automated Hargreaves device (References 28 and 41) requires that a constant intensity, radiant heat source be aimed at the midplantar area of an animals paw and the latency of response time from initial heat source activation until paw withdrawal is recorded with an automatic timer. Mechanical allodynia is the measure of foot withdrawal in response to normally innocuous mechanical stimuli using a graded series of von Frey hairs (Reference 42). Each graded hair represents an increasing force in grams applied to the extremity. Our laboratory now utilizes an automated von frey device for mechanical allodynia measurement. These behavioral measures of allodynia and hyperalgesia are the most commonly used measures for pain in a variety of animal and human models, including neuropathic pain after spinal injections of quisqualic acid (References 19, 36, and 40).

Test Results from Human Cloned Cell Lines

EXAMPLE 1

Serotonergic NT2 Cell Line in Vitro—a Unique Serotonin hNT2 Cell Line (FIGS. 1A-D)

Figure 1B:
FIG. 1B is a phase-contrast photomicrograph of differentiated (two week) hNT2.19 cells.
Figure 1C:
FIG. 1C is a photomicrograph of a sample of two-week differentiated hNT2.19 cells stained for an antibody directed against serotonin (5HT)
Figure 1D:
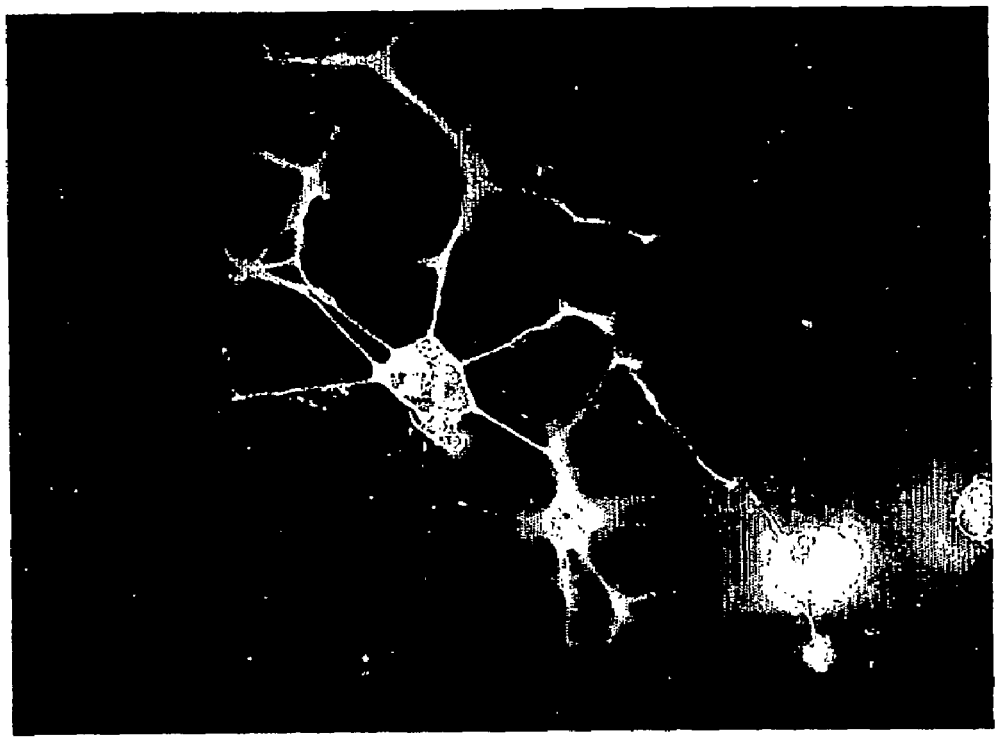
FIG. 1D is a photomicrograph of another sample of hNT2.19 cells stained in the same manner as the cells of FIG. 1C.

The hNT2.19 serotonergic cell line, was subcloned by serial dilution and treated for two weeks with retinoic acid and mitotic inhibitors. They were further differentiated for two weeks before an antibody stain for serotonin (5HT). The 5HT NT2.19 cells, have a very large nucleus, are generally multipolar, with short neurites and stain brightly for 5HT. FIG. 1A is a phase-contrast photomicrograph of differentiated (one week) hNT2.19 cells; FIG. 1B is the same cells differentiated two weeks in culture. FIG. 1C is a sample of 2 week differentiated hNT2.19 cells stained for an antibody directed against serotonin (5HT); FIG. 1D is another photomicrograph of another hNT2.19 cell similarly stained.

EXAMPLE 2

The GABAergic NT2 Cell Line In Vitro—a Unique Neuronal GABA hNT2 Cell Line (FIGS. 2A-H)

Figure 2A:
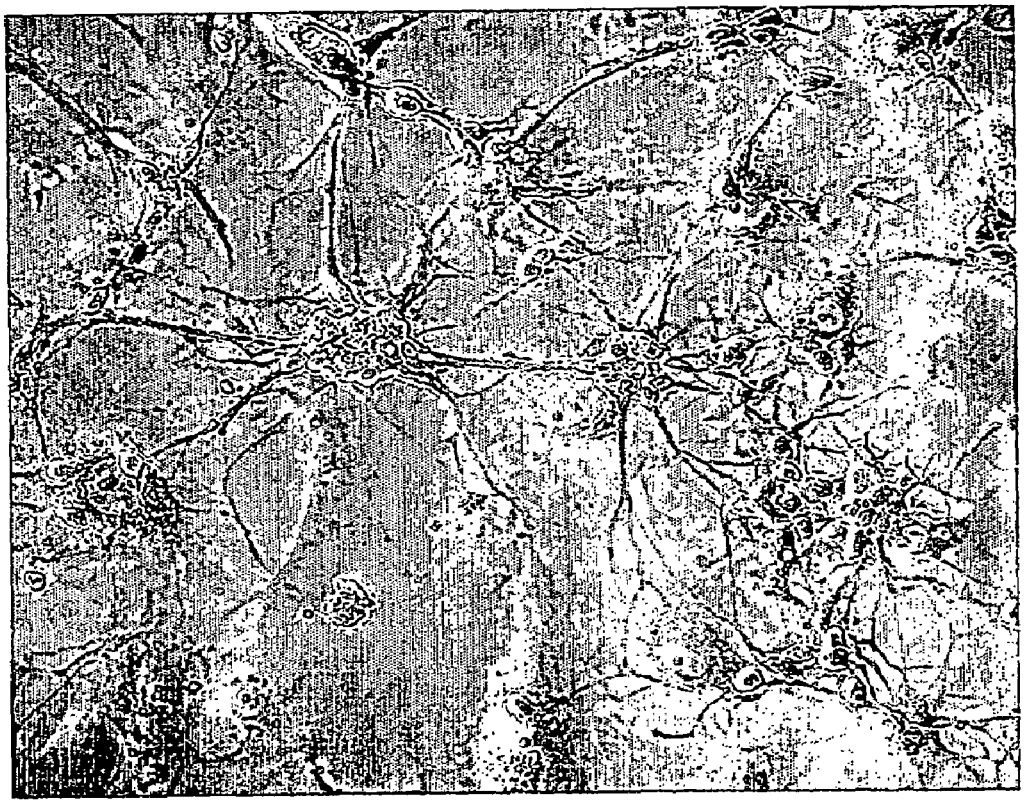
FIG. 2A is a phase-contrast photomicrograph of differentiated (one week) hNT2.17 cells.
Figure 2B:
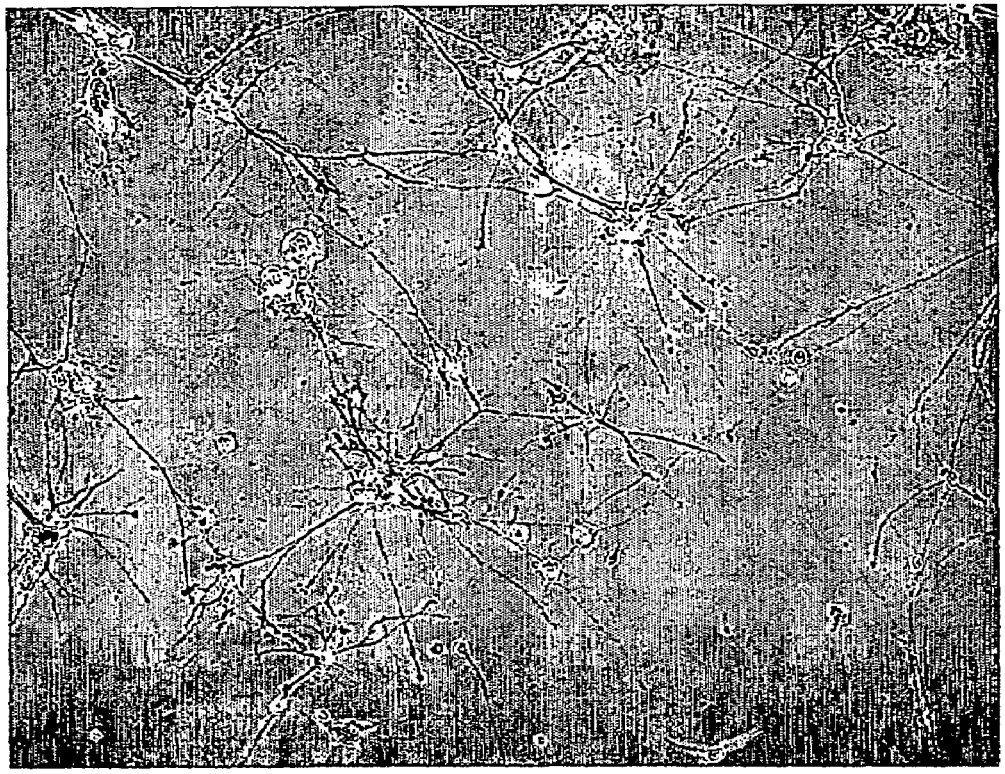
FIG. 2B is a phase-contrast photomicrograph of differentiated (two week) hNT2.17 cells.
Figure 2C:
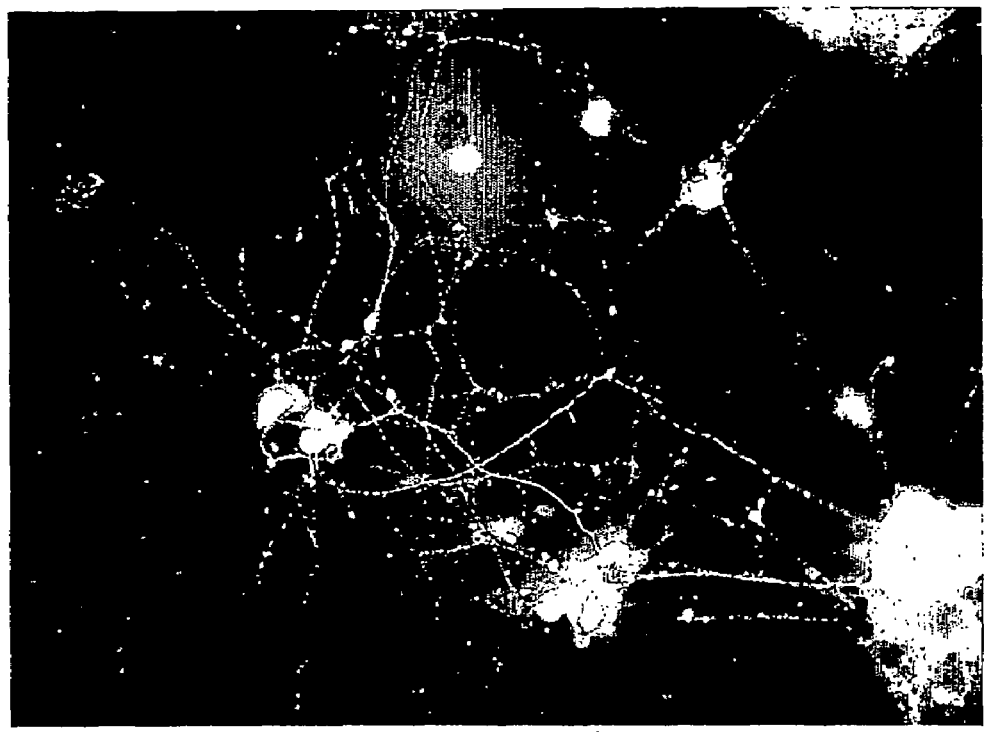
FIG. 2C is a photomicrograph of a sample of two-week differentiated hNT2.17 cells stained for an antibody directed against GABA.
Figure 2D:
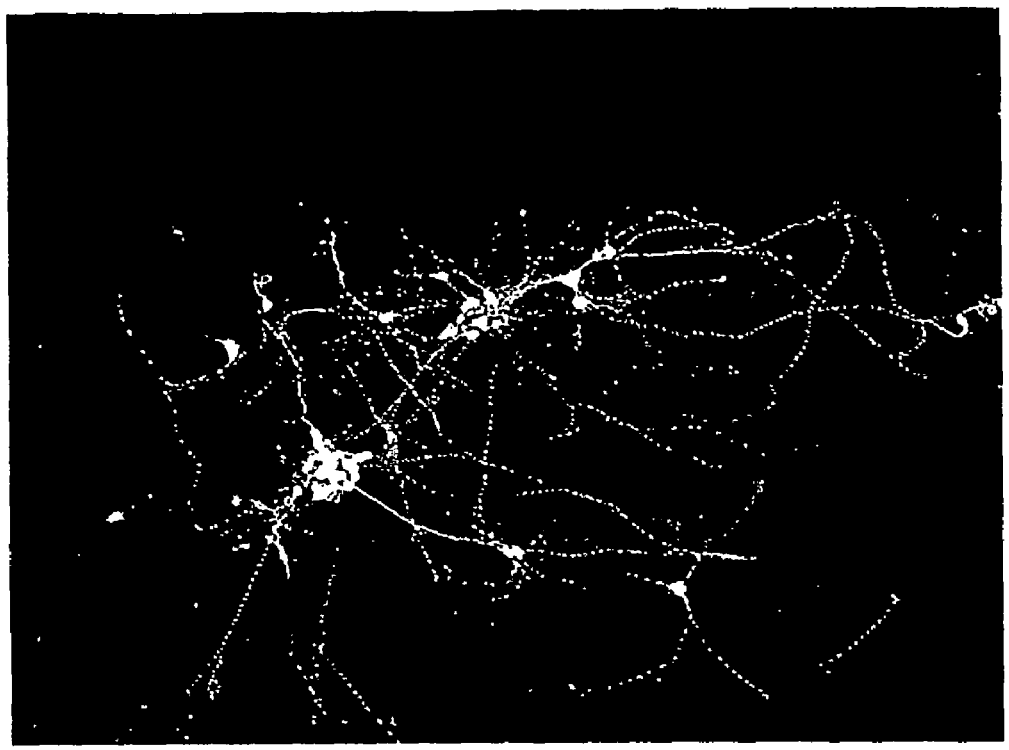
FIG. 2D is a photomicrograph of another sample of hNT2.17 cells stained in the-same manner as the cells of FIG. 2C.
Figure 2E:
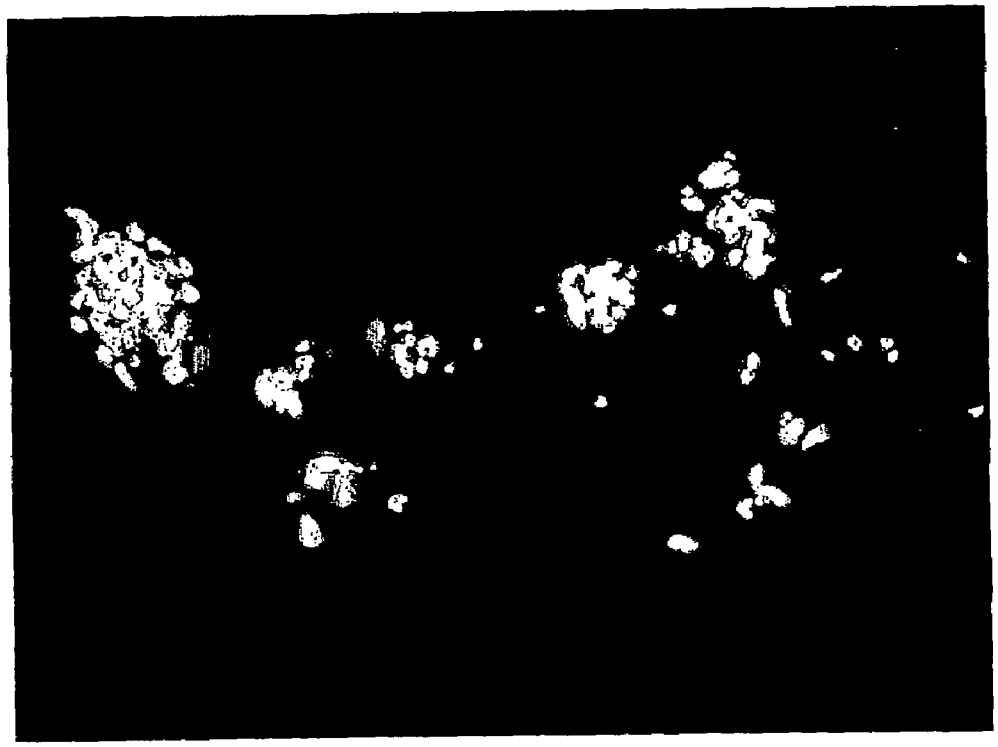
FIG. 2E is a photomicrograph of hNT2.17 cells, differentiated two-weeks and stained with the nuclear marker DAPI to illustrate viable cells.
Figure 2F:
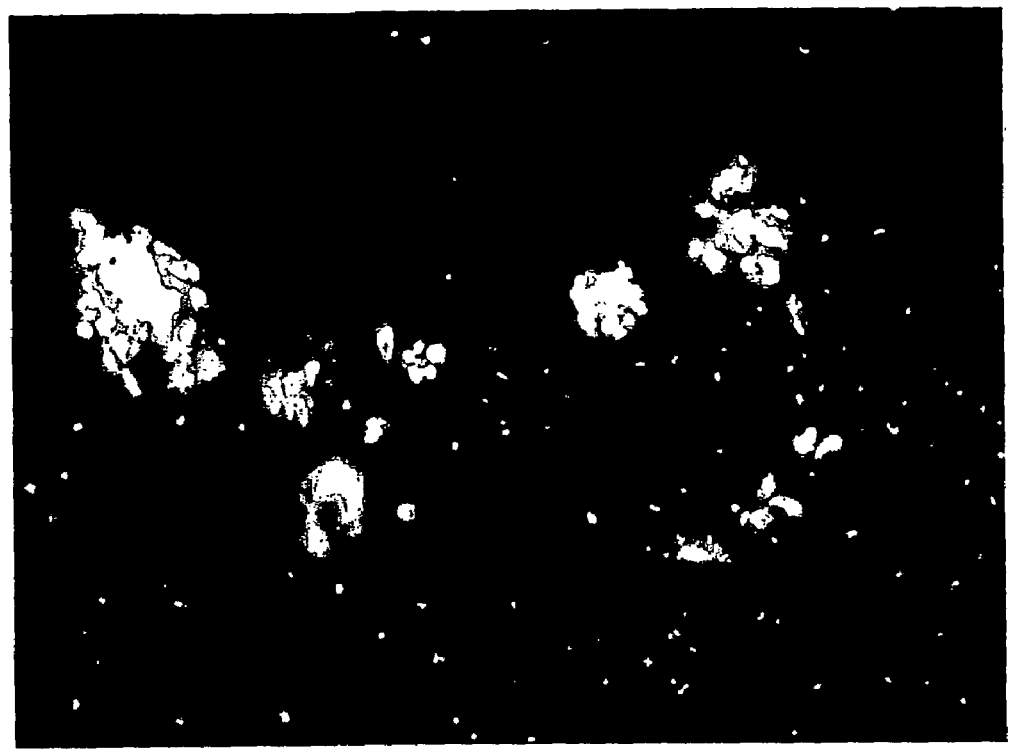
FIG. 2F is a photomicrograph of the same culture of cells shown in FIG. 2E, co-labeled for the neuronal marker NeuN.
Figure 2G:
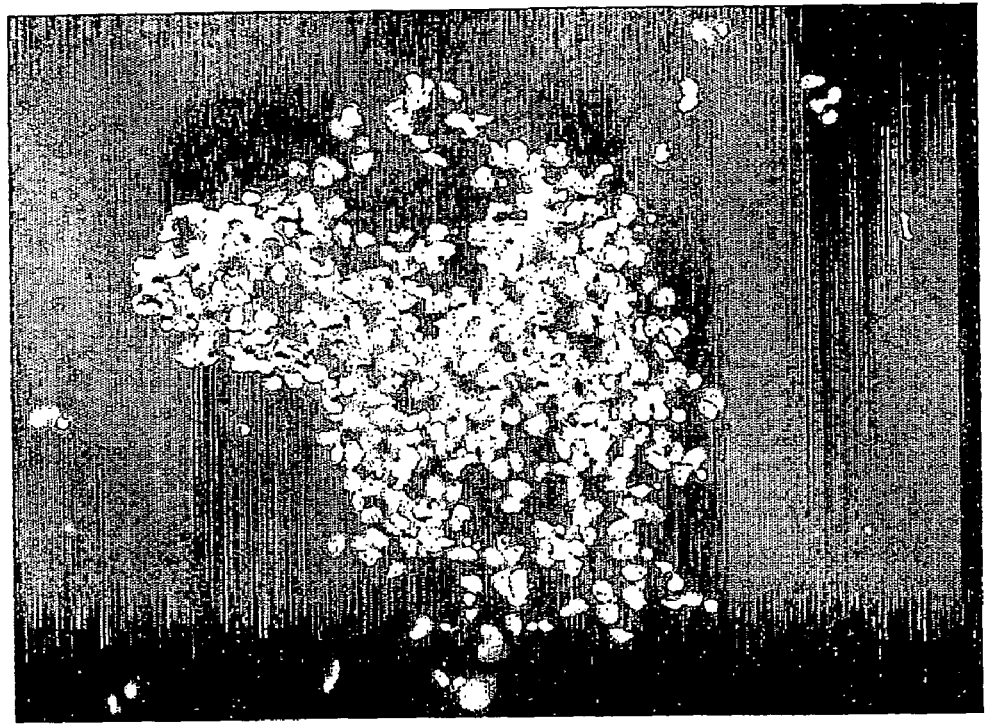
FIG. 2G is a photomicrograph of another sample of two-week differentiated culture of hNT2.17 cells stained with DAPI to illustrate viability.
Figure 2H:
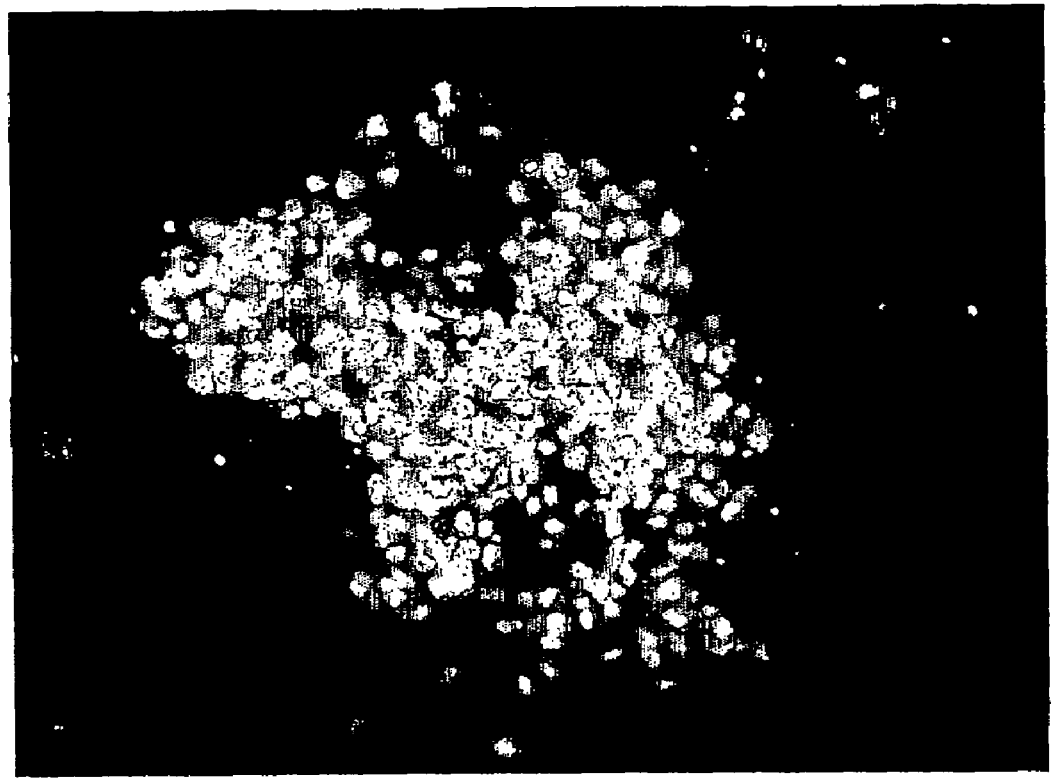
FIG. 2H is a photomicrograph of the same culture of cells shown in FIG. 2G, co-labeled for the human marker NuMA.

Another cloned hNT2 cell line, hNT2.17, which is positive for GABA was subcloned by serial dilution and treated for two weeks with retinoic acid and mitotic inhibitors. They were further differentiated for two weeks before an antibody stain for GABA. The GABA NT2.17 cell line has small nuclei, extensive multipolar or bipolar neurites and stains brightly for GABA (FIGS. 2C and D). Other cultures of hNT2.17, differentiated for 2 weeks, were also stained for the neuronal marker, NeuN (FIG. 2F), and the human nuclear matrix antigen (NuMA) marker in vitro (FIG. 2H). The counterstain DAPI, identifies viable, surviving cell grafts. These markers, especially human NuMA, can be used to specifically identify hNT2 grafts in vivo after transplant in the rat. FIG. 2A is a phase-contrast photomicrograph of differentiated (one week) hNT2.17 cells; FIG. 2B is the same hNT2.17, cells differentiated two weeks in culture. FIG. 2C is a sample of 2 week differentiated hNT2.17 cells stained for an antibody directed against GABA; FIG. 2D is another photomicrograph of another hNT2.17 cell similarly stained for GABA; FIG. 2E is a photomicrograph of hNT2.17 cells, differentiated 2 weeks and stained with DAPI to illustrate viable cells; FIG. 2F is the same culture co-labeled for the neuronal marker NeuN. FIG. 2G is another 2 week differentiated culture of hNT2.17 cells again stained with DAPI to illustrate viability; FIG. 2H is the same culture co-labeled for the human marker NuMA.

EXAMPLE 3

Figure 3:
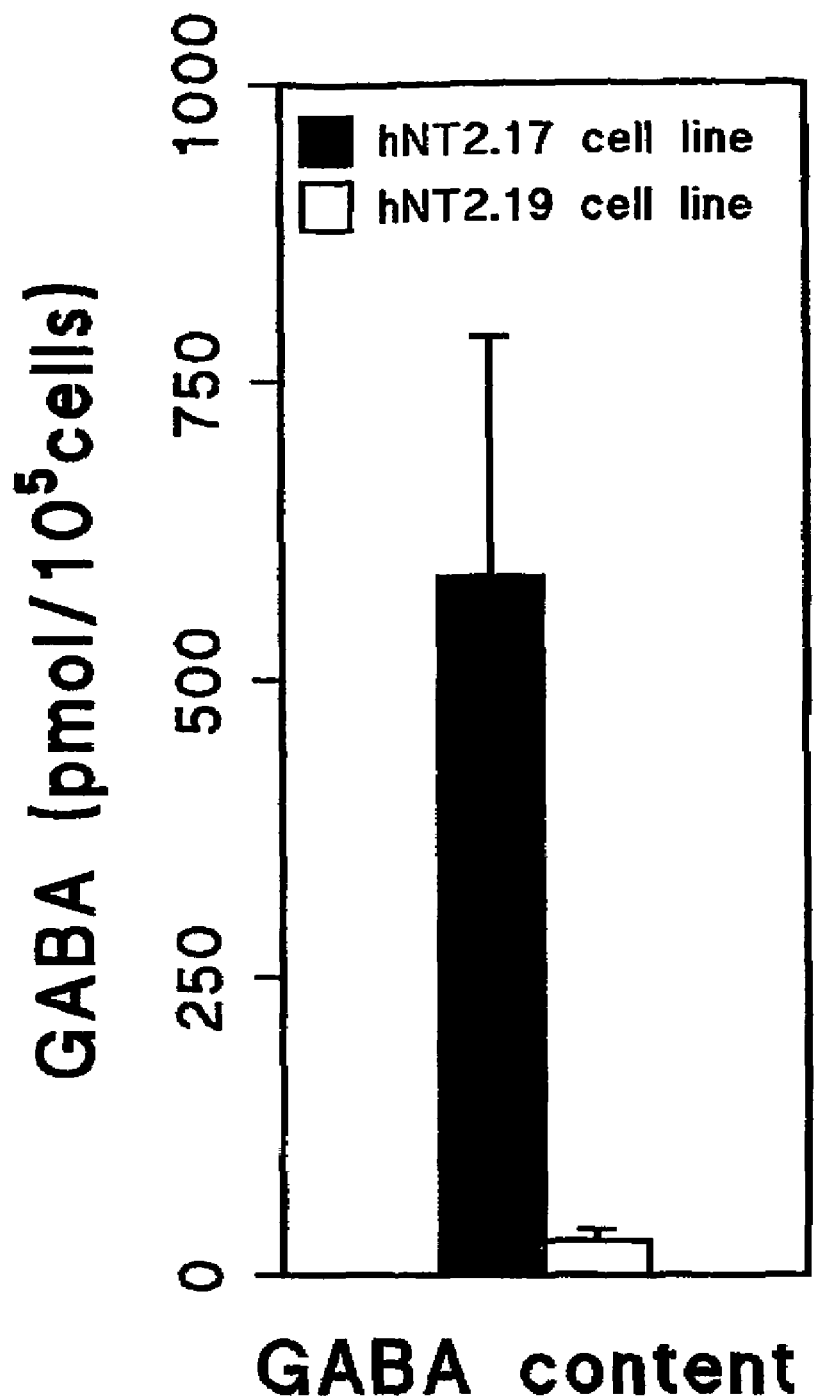
FIG. 3 is a bar chart showing GABA synthesis in two-week differentiated hNT2.17 and hNT2.19 cell lines in vitro.

GABA Content (Synthesis) in hNT2.17 and hNT2.19 Cell Lines In Vitro—Only hNT2.17 Cells Synthesize GABA (FIG. 3)

Both the hNT2.17 and hNT2.19 cell lines were differentiated, after retinoic acid and mitotic inhibitor treatment, for two weeks in 6-well substrate-coated plates before cell lysis and examination of cell content for authentic GABA synthesis by HPLC methods (described above). Only the hNT2.17 cell line had any significant GABA content, matching the immunohistochemical staining patterns seen above. The hNT2.19 cells, which had stained for 5HT, not GABA, had no significant GABA content examined by HPLC methods.

EXAMPLE 4

Figure 4A:
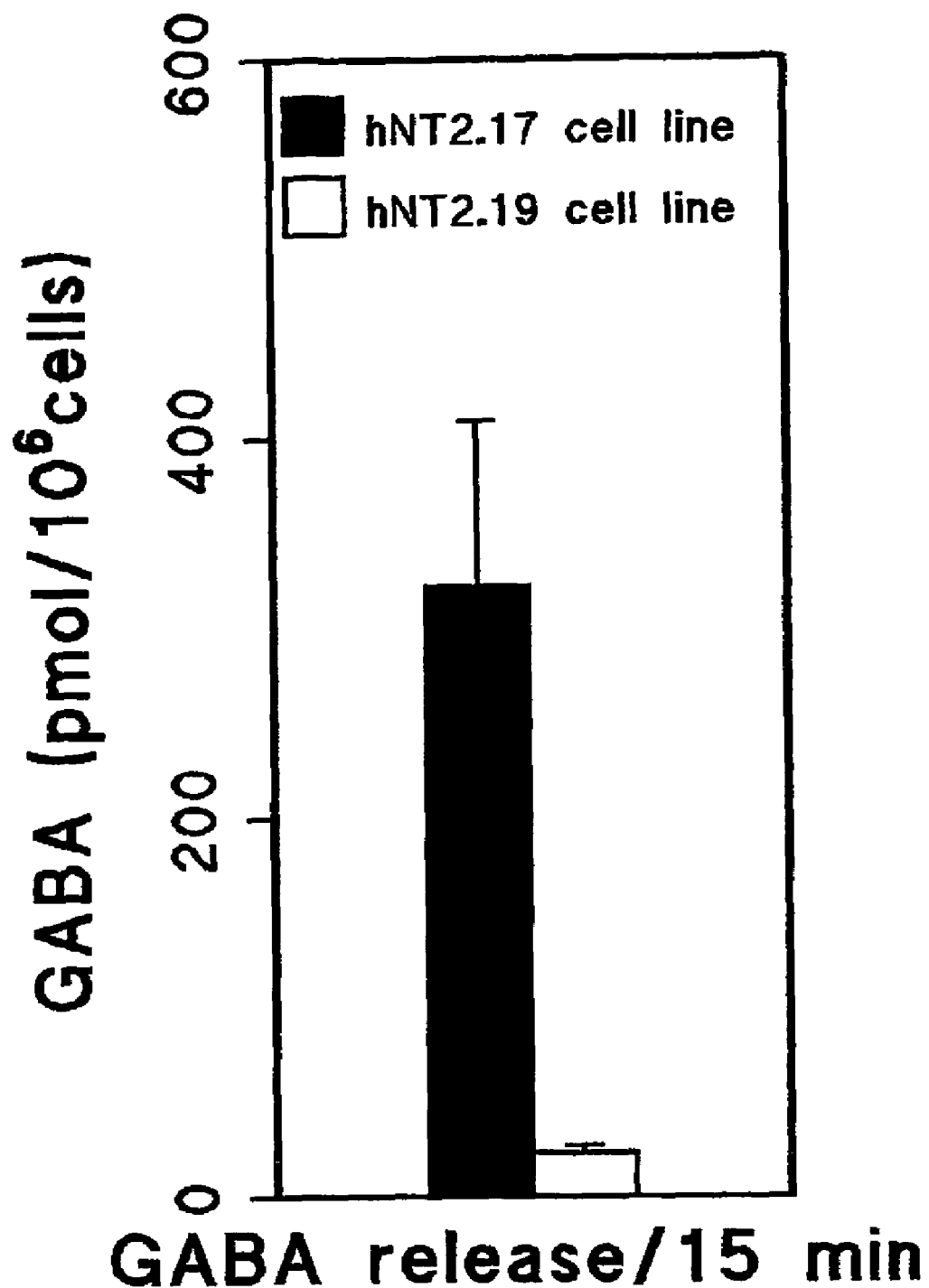
FIGS. 4A-4B are bar charts showing GABA release, stimulated by low (FIG. 4A) or high concentrations (FIG. 4B) of K+ in hNT2.17 and hNT2.19 cell lines in vitro.
Figure 4B:
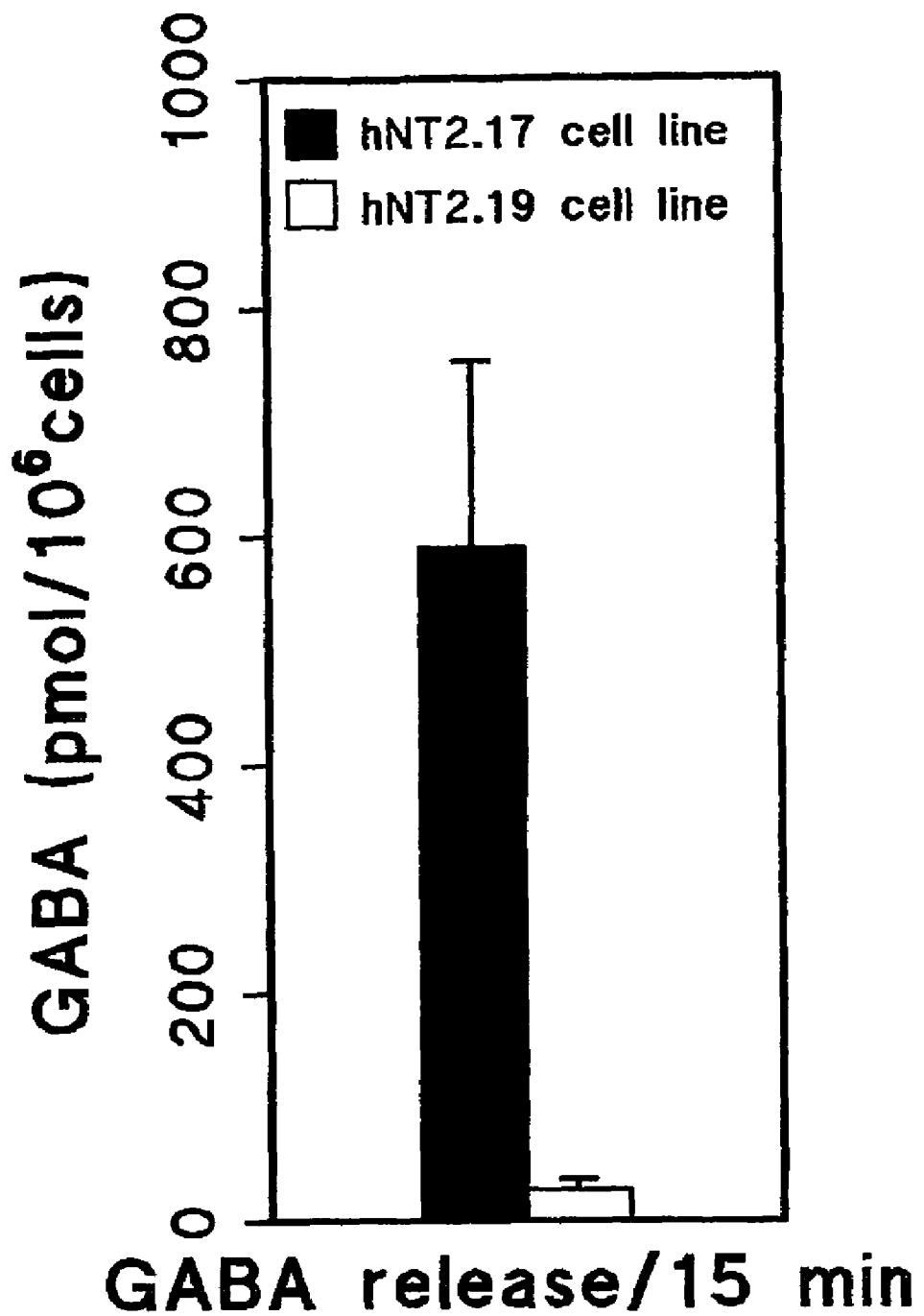

GABA Release in hNT2.17 and hNT2.19 Cell Lines In Vitro—Only hNT2.17 Cells Release GABA (FIGS. 4A-B)

As above, both the hNT2.17 and hNT2.19 cell lines were differentiated, after retinoic acid and mitotic inhibitor treatment, for two weeks in 6-well substrate-coated plates before cells were exposed to normal (2.95 mM; FIG. 4A) or high (100 mM; FIG. 4B) concentrations of KCl for potassium (K+)-stimulated release for authentic GABA by HPLC methods. Only the hNT2.17 cell line had any significant GABA release, matching the immunohistochemical staining pattern seen above. The hNT2.19 cells, which had stained for 5HT, not GABA, had little detectable GABA release examined by HPLC methods.

EXAMPLE 5

Transplant of hNT2.17 and hNT2.19 Cell Lines in a Model of Spasticity: Pain and Spasticity Behaviors—only hNT2.17 Cells Reverse Spasticity Behaviors, but Both hNT2.17 and hNT2.19 Reverse Thermal Hyperalgesia in the Affected Extremity After Complete Spinal Transection (FIGS. 5A-F)

Figure 5A:
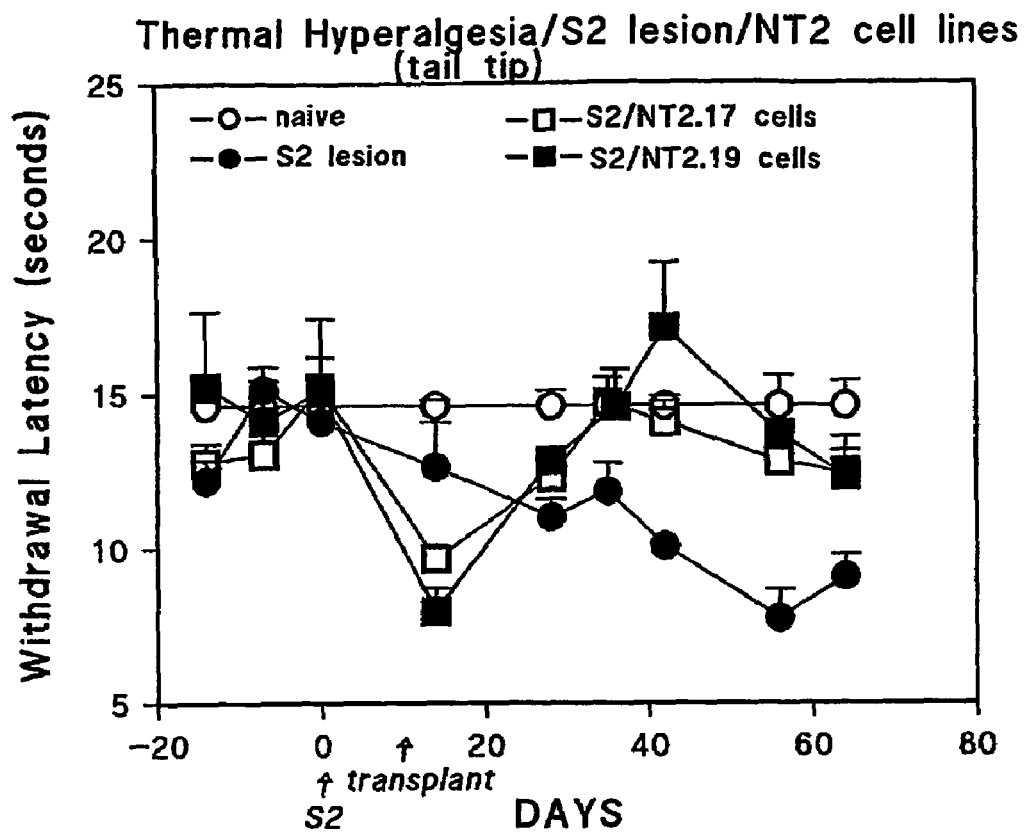
FIG. 5A is a graphical illustration showing reversal of thermal hyperalgesia (tail-flick) in rats by hNT2.17 and hNT2.19 cells, where cells were grafted after complete sacral transection (S2)
Figure 5B:
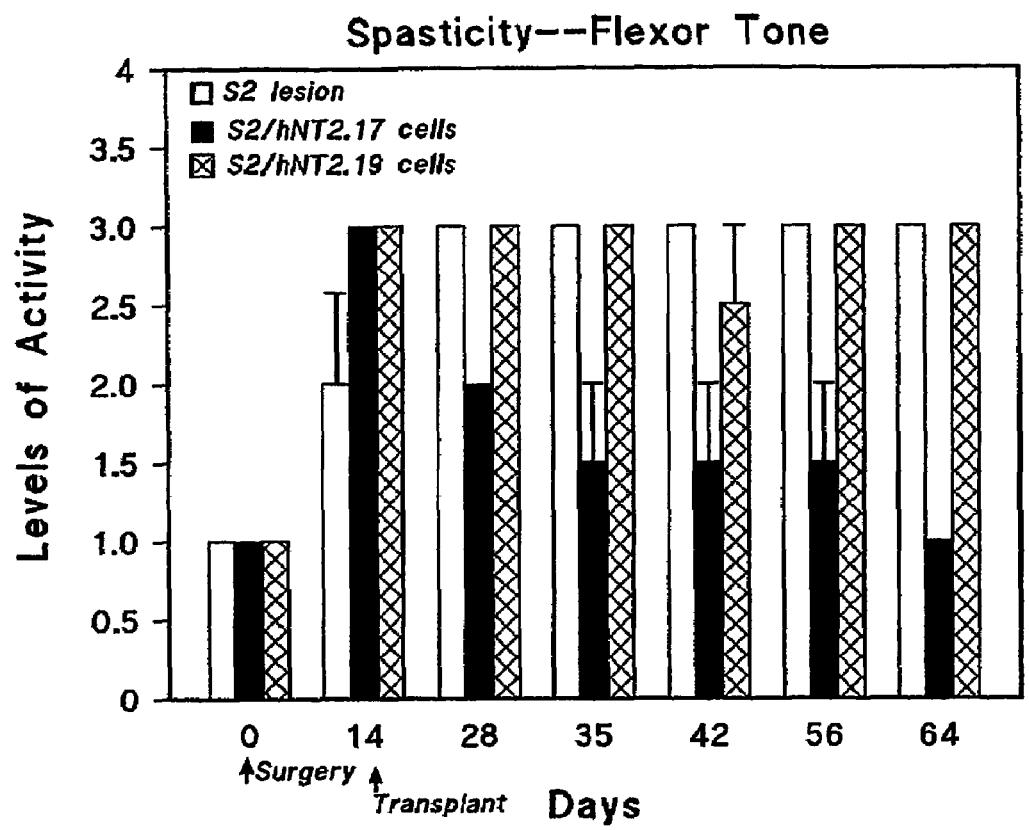
FIG. 5B is a bar chart illustrating spasticity (flexor tone) following S2 lesion and transplant of either hNT2.17 or hNT2.19 cells.
Figure 5C:
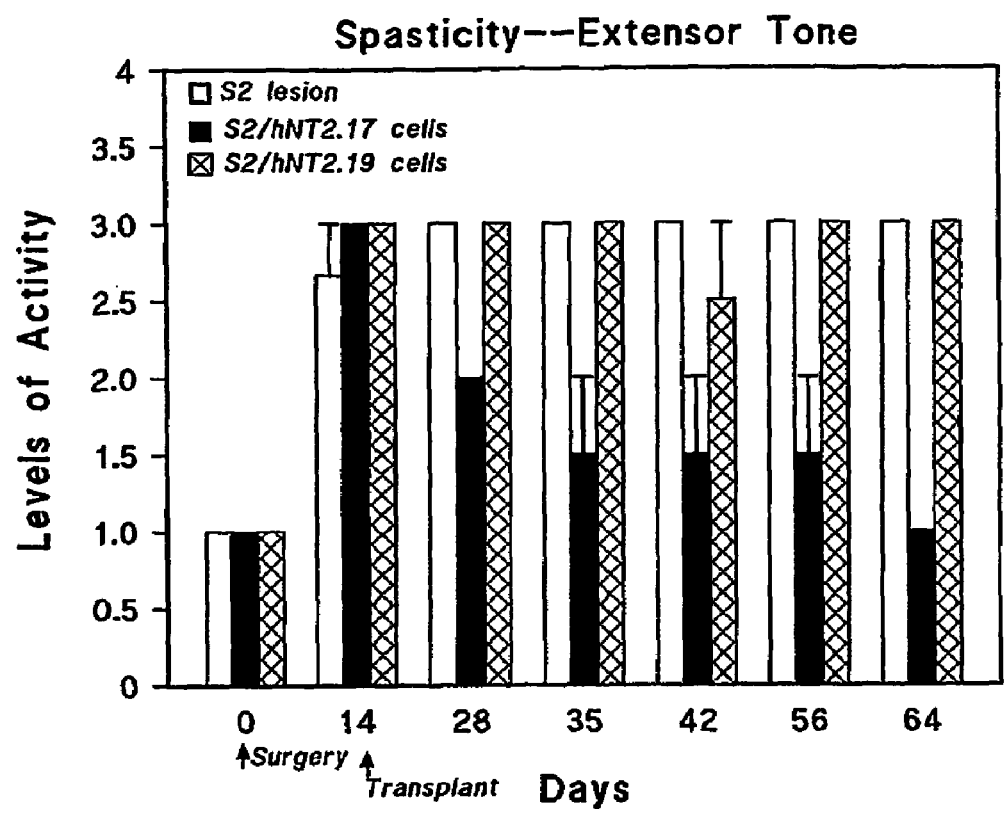
FIG. 5C is a bar chart illustrating spasticity (extensor tone) following S2 lesion and transplant of either hNT2.17 or hNT2.19 cells.
Figure 5D:
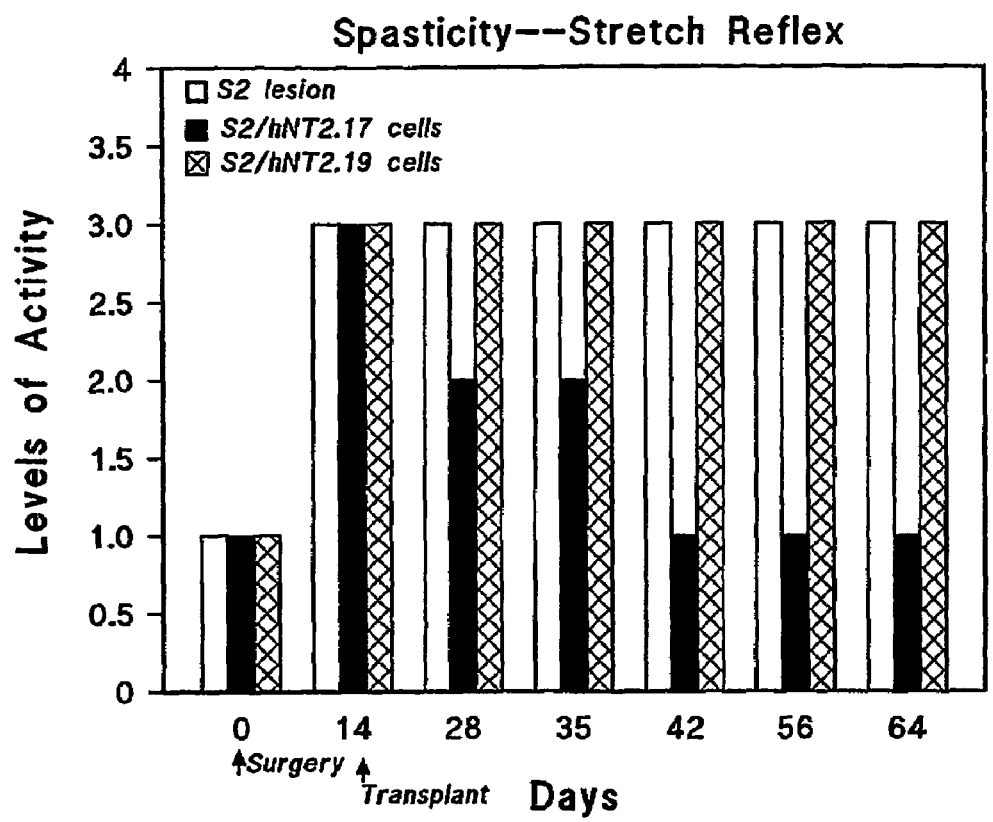
FIG. 5D is a bar chart illustrating spasticity (stretch reflex) following S2 lesion and transplant of either hNT2.17 or hNT2.19 cells.
Figure 5E:
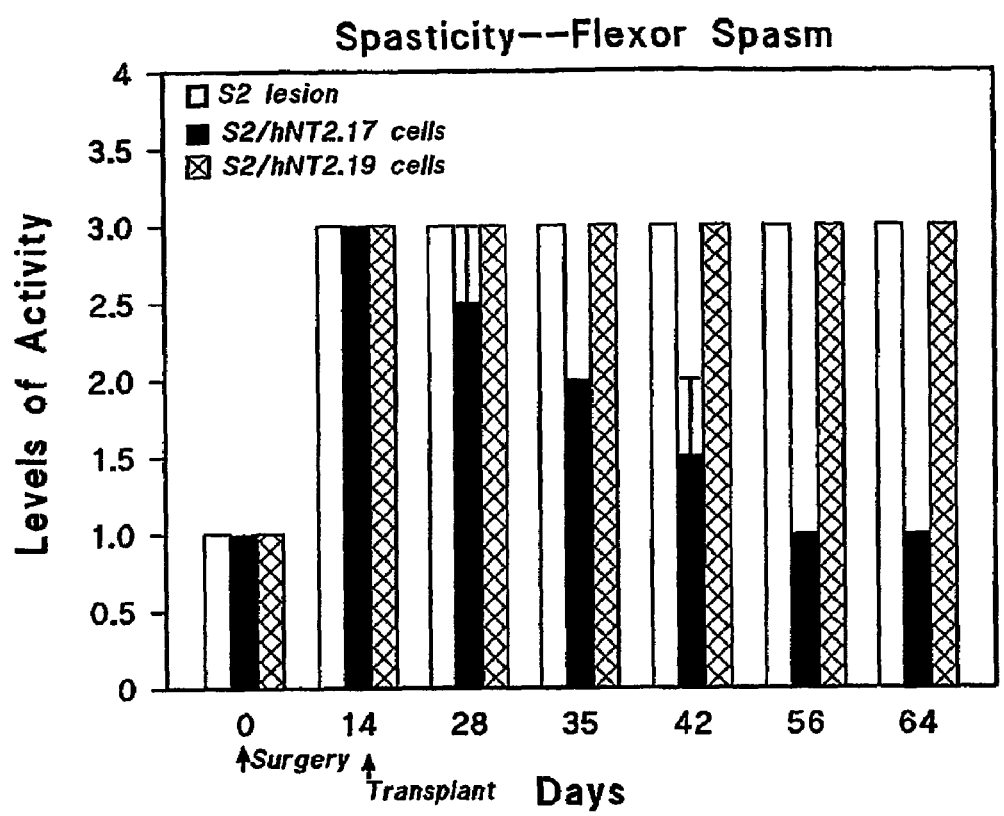
FIG. 5E is a bar chart illustrating spasticity (flexor spasm) following S2 lesion and transplant of either hNT2.17 or hNT2.19 cells.
Figure 5F:
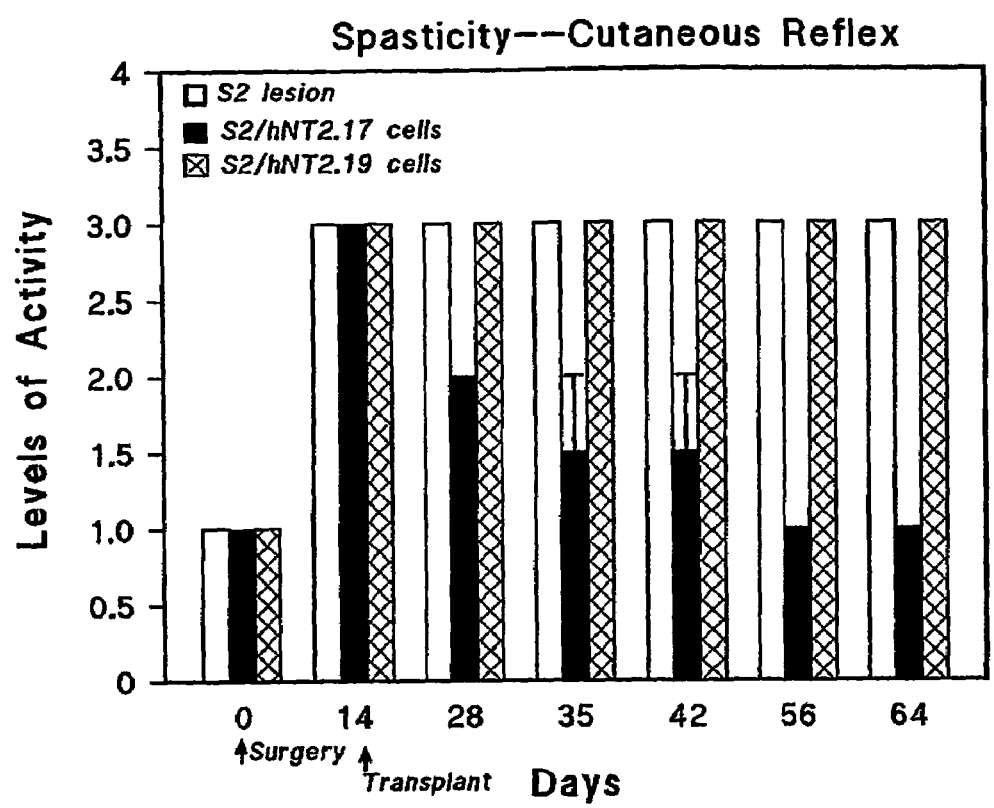
FIG. 5F is a bar chart illustrating spasticity (cutaneous reflex) following S2 lesion and transplant of either hNT2.17 or hNT2.19 cells.

Adult male Wistar Furth rats were given a sacral (S2) complete spinal transection in a rat model of spasticity (Reference 26) and either examined for spasticity behaviors without cell transplants, or given subarachnoid transplants of hNT2.17 or hNT2.19 cells ($10^6$ cells/injection) which had been differentiated for two weeks in vitro. The transplant was done at two weeks (14 days) after the original S2 lesion (surgery). All animals were examined for spasticity behaviors and thermal hyperalgesia (heat sesnsitivity) in the tail-tip and musculature. In FIG. 5A, thermal hyperalgesia was measured weekly at the tail tip after the S2 lesion (day 0), and after the S2 lesion, followed by cell grafts at 2 weeks after S2 injury, until about 65 days after the SCI. Both hNT2.17 and hNT2.19 reversed the thermal hyperalgesia induced by the S2 transection, since this is a measure of the development of chronic pain and hypersensitivity to noxious thermal stimuli. However, when spasticity behaviors are examined following the S2 lesion (FIGS. 5B-F), only the grafts of the GABA-secreting hNT2.17 cells tended to reverse/reduce the spasticity behaviors (listed on the top of each graph). Serotonin from the grafts of hNT2.19 cells had no effect on these spasticity behaviors, and these cells function as the negative control transplant for the GABA cells.

EXAMPLE 6

Transplant of hNT2.17 and hNT2.19 Cell Lines in a Model of Excitotoxic SCI and Chronic Pain: Immunohistochemistry—both hNT2.17 and hNT2.19 Survive Greater than 6 Weeks after Transplant in a Model of SCI (FIGS. 6A-D)

Figure 6A:
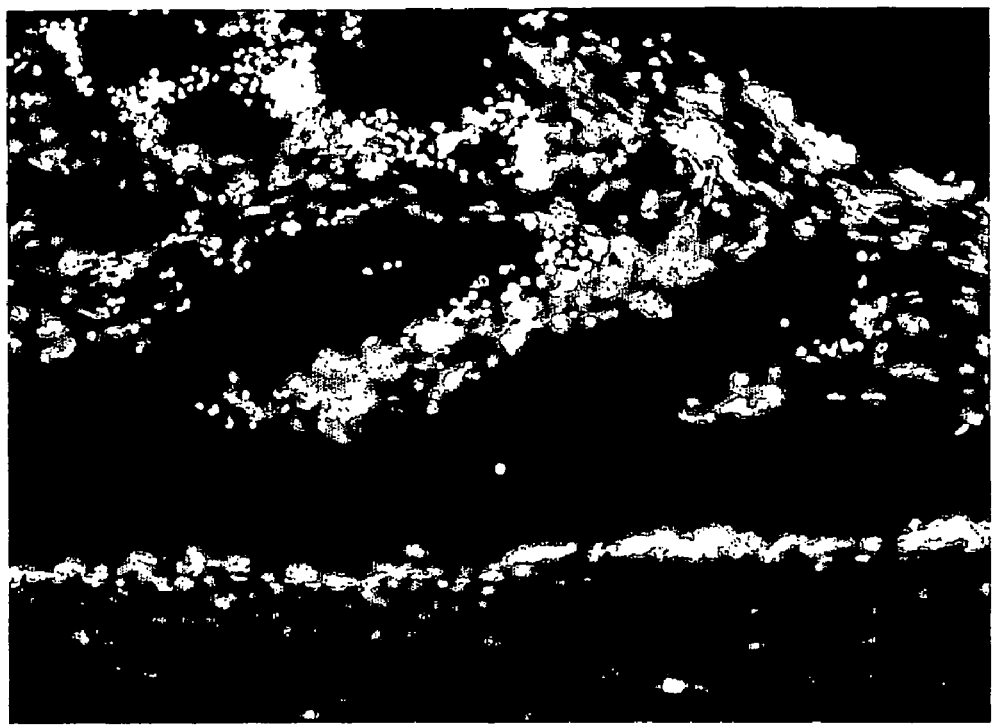
FIG. 6A is a photomicrograph illustrating surviving and viable (DAPI positive) hNT2.19 grafted cells on the spinal cord after excitotoxic SCI.
Figure 6B:
FIG. 6B is a photomicrograph illustrating surviving and viable (DAPI positive) hNT2.19 grafted cells co-labeled for the human marker NuMA after excitotoxic SCI.
Figure 6C:
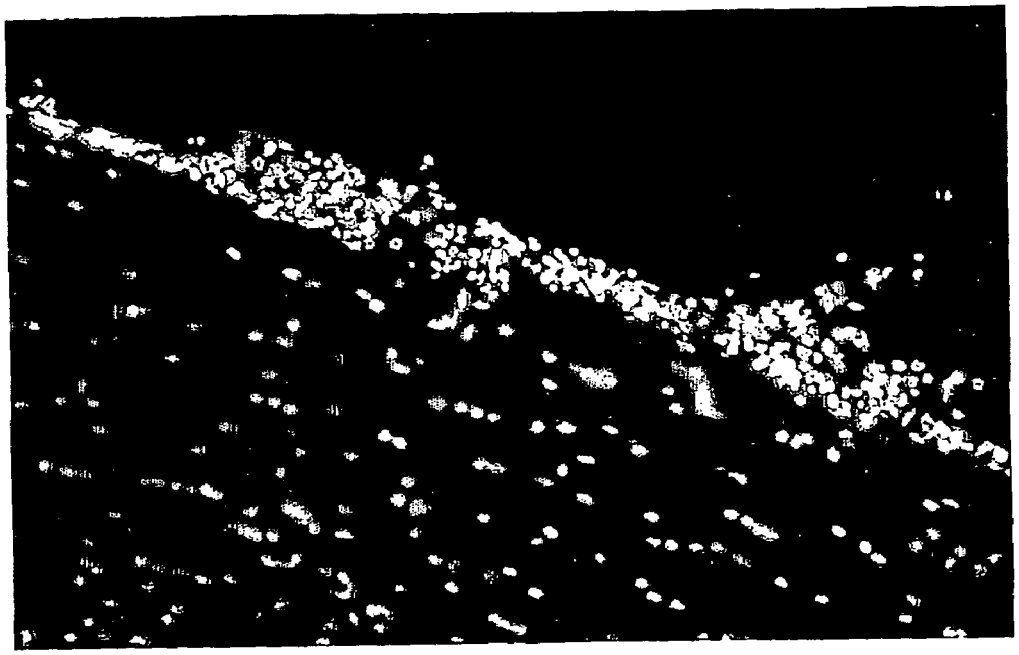
FIG. 6C is a photomicrograph illustrating surviving and viable (DAPI positive) hNT2.17 grafted cells on the spinal cord after excitotoxic SCI.
Figure 6D:
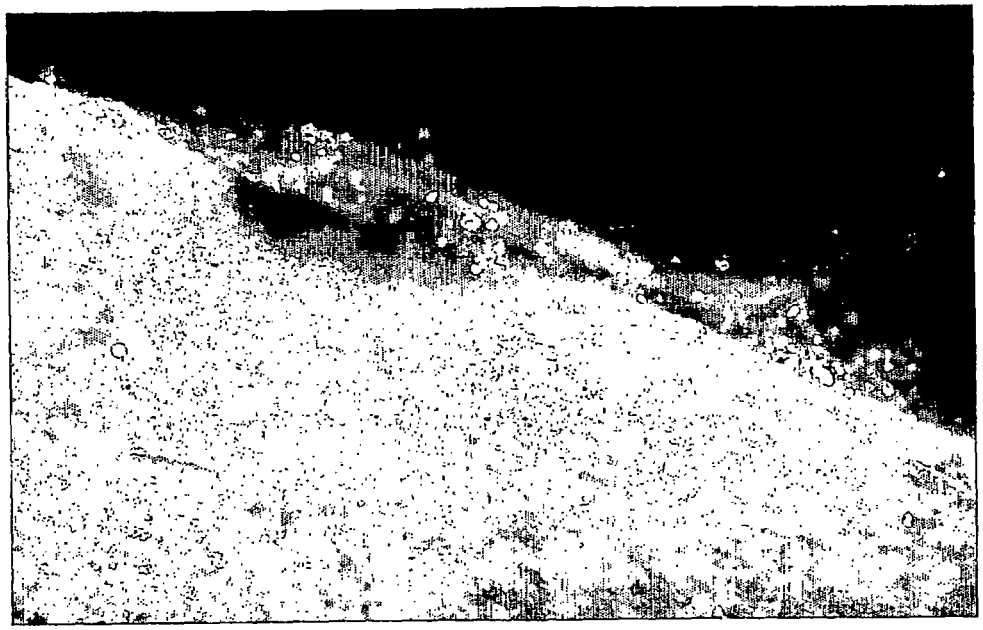
FIG. 6D is a photomicrograph illustrating surviving and viable (DAPI positive) hNT2.17 grafted cells co-labeled for the human marker NuMA after excitotoxic SCI.

Adult male Wistar Furth rats were spinally injected with an excitoxic agent, quisqualic acid in a rat model of SCI and chronic pain (References 29, 38, 43, and 44) and spinal cord sections were examined at 60 days after QUIS for evidence of surviving hNT2.17 and hNT2.19 cell line grafts. Either hNT2.17 or hNT2.19 cells ($10^6$ cells/injection), which had been differentiated for two weeks in vitro, were injected into the subaracnoid space two weeks (14 days) after the QUIS lesion. Cell graft sites were co-localized with DAPI and the human marker NuMA (FIGS. 6A-D). There are many surviving hNT2.17 and hNT2.19 grafted cells visible on the pial surface, which stain for the human-specific marker NuMA at the end of the experiment, 60 days after QUIS and about 6 weeks after cell transplant. FIG. 6A illustrates surviving and viable (DAPI positive) hNT2.19 grafted cells on the cord; FIG. 6B the same grafted hNT2.19 cells are co-labeled for the human marker NuMA. FIG. 6C illustrates surviving and viable (DAPI positive) hNT2.17 grafted cells on the cord; FIG. 6D the same grafted hNT2.17 cells are co-labeled for the human marker NuMA.

EXAMPLE 7

Figure 7A:
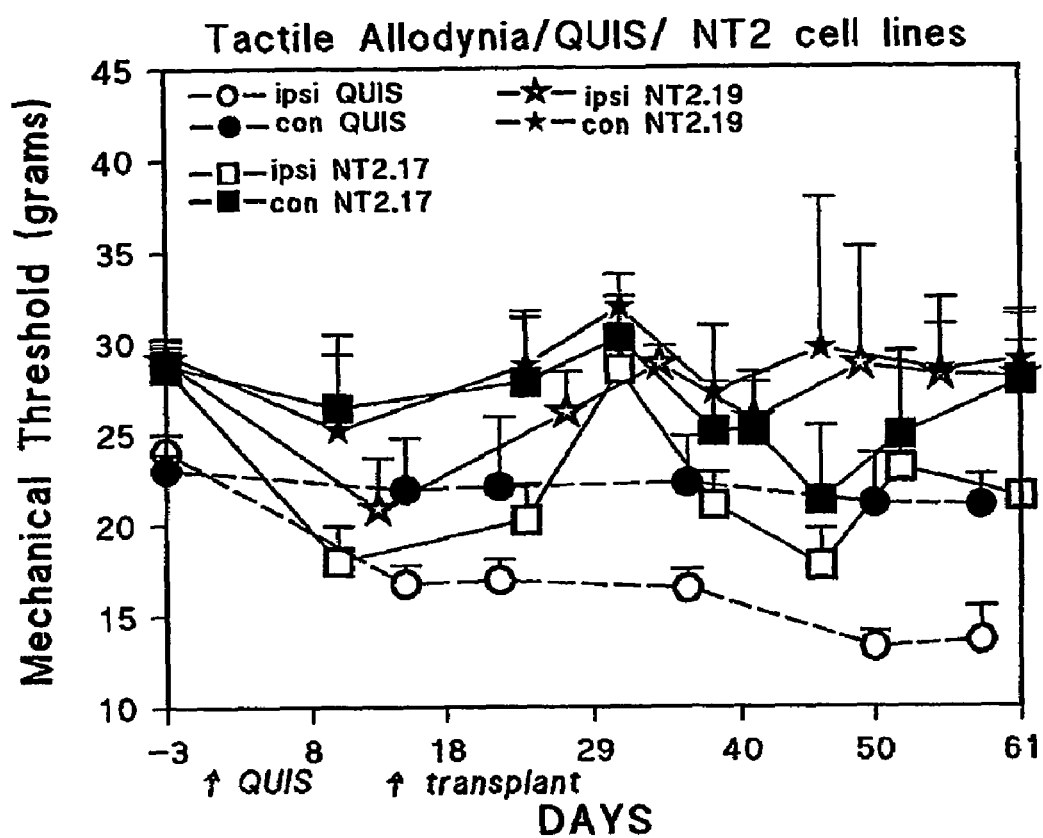
FIG. 7A is a graphical illustration showing reduction/reversal of tactile hypersensitivity in a model of excitotoxic SCI pain.
Figure 7B:
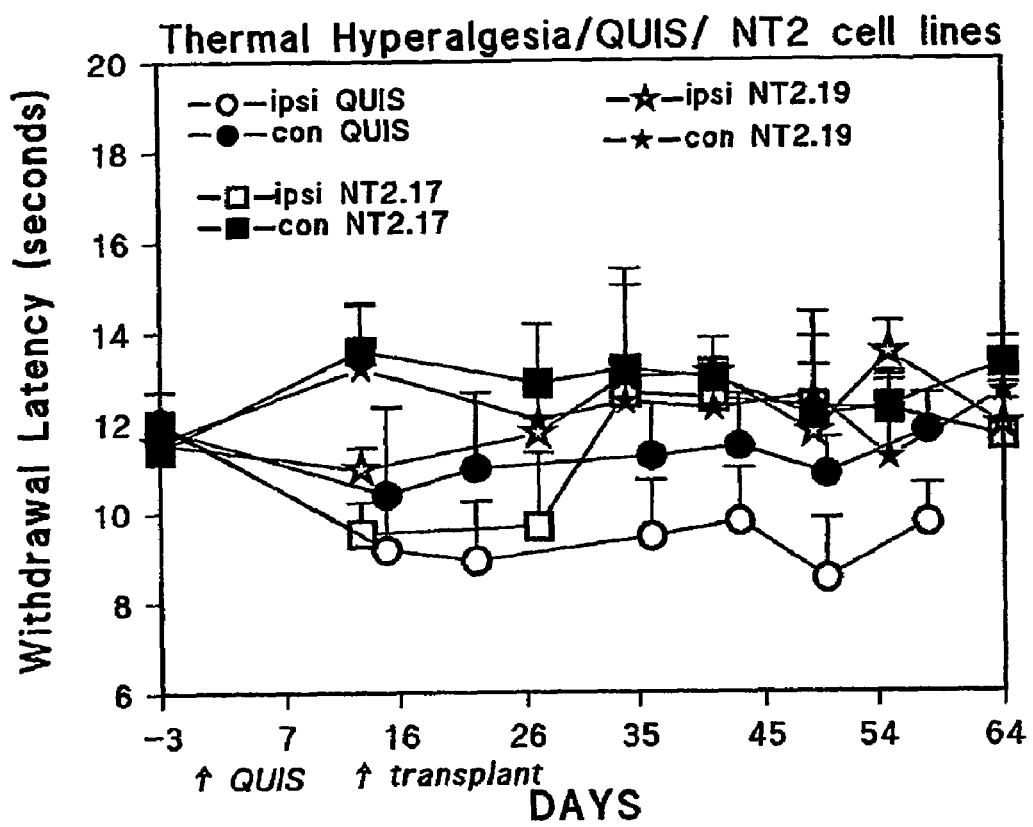
FIG. 7B is a graphical illustration showing reduction/reversal of thermal hyperalgesia in a model of excitotoxic SCI pain.

Transplant of hNT2.17 and hNT2.19 Cell Lines in a Model of Excitotoxic SCI and Chronic Pain: Sensory Behaviors—both hNT2.17 and hNT2.19 Cell Grafts Reduce/Reverse Thermal and Tactile Hypersensitivity in a Model of SCI Pain (FIGS. 7A-B)

Adult male Wistar Furth rats were spinally injected with an excitoxic agent, quisqualic acid in a rat model of SCI and chronic pain (References 29, 38, 43, and 44), animals are either left untreated or injected with either hNT2.17 or hNT2.19 cells ($10^6$ cells/injection) into the subarachnoid space at two weeks (14 days) after QUIS. Animals were tested before the SCI (baseline) and twice a week following QUIS and cell grafts for hypersensitivity to tactile or thermal stimuli in hindpaws below the SCI. All animals were examined for chronic pain behaviors in the contralateral (con) and ipsilateral (ipsi) hindpaws. Both ipsilateral and contralateral hindpaws recovered near-normal sensory responses to tactile and thermal stimuli after grafting either the GABAergic hNT2.17 or serotonergic hNT2.19 cells, compared to the QUIS injury alone (measure of behaviors described above). QUIS injury negatively affects hindpaw responses bilaterally, but the ipsilateral hindpaw is most affected by the injection of quisqualic acid. Neither hindpaw recovers normal tactile or thermal responses after QUIS alone by 60 days after the injection.

A pharmaceutical composition including an isolated or cloned human cell line expressing serotonin (5HT) or gamma-aminobutyric acid (GABA), may be prepared, in a conventional manner. In particular, a pharmaceutical composition made in accordance with the present invention would include an isolated or cloned human cell expressing serotonin (5HT) or gamma-aminobutyric acid (GABA), in an amount sufficient to provide therapeutic and/or prophylactic benefit, in combination with one or more pharmaceutically or physiologically acceptable carriers, diluents or excipients. Compositions of the present invention may be formulated for any appropriate manner for administration, including, for example, nasal, intravenous or intramuscular administration, or nervous system or non-nervous system transplantation. Appropriate dosages, duration and frequency of administration would be determined by known factors, such as the condition of the patient, the type and severity of the disease and the method of administration.

The hNT2.17 and hNT2.19 cell lines were deposited under the Budapest Treaty with the American Type Culture Collection (ATCC), located at 10801 University Blvd., Manassas, Va. 20110-2209, on Oct. 12, 2005, under Accession Nos. PTA-7154 and PTA-7153, respectively.

While this invention has been described as having preferred sequences, ranges, steps, materials, or designs, it is understood that it includes further modifications, variations, uses and/or adaptations thereof following in general the principle of the invention, and including such departures from the present disclosure as those come within the known or customary practice in the art to which the invention pertains, and as may be applied to the central features hereinbeforesetforth, and fall within the scope of the invention and of the limits of the appended claims.

The following references, to the extent that they provide exemplary procedural or other details supplementary to those set forth herein, are specifically incorporated herein by reference.

REFERENCES

1. Berg-Johnsen J, Roste G, Solgaard T, Lundar T. Continuous intrathecal infusion of baclofen. A new therapeutic method for spasticity. Tidsskr Nor Laegeforen 1998; 118: 3256-3260.
2. Kuraishi Y, Hirota N, Satoh M, Takagi H. Antinociceptive effects of intrathecal opioids, noradrenaline and serotonin in rats: mechanical and thermal algesic tests. Brain Res 1985;326: 168-171.
3. Fakhoury T, Abou-Khalil B, Blumenkopf B. EEG changes in intrathecal baclofen overdose: a case report and review of the literature. Electroencephalogr Clin Neurophysiol 1998; 107: 339-342.
4. Postma T J, Oenema D, Terpstra S, Bouma J. Cost analysis of the treatment of severe spinal spasticity with a continuous intrathecal baclofen infusion system. Pharmacoeconomics 1999;15: 395-404.
5. Zed P J, Stiver H G, Devonshire V, Jewesson P J. Continuous intrathecal pump infusion of baclofen with antibiotic drugs for treatment of pump-assocated meningitis. Case report. J Neurosurg 2000;92: 347-349.
6. Gock S B, Wong S H, Stormo K A, Jentzen J M. Self-intoxication with morphine obtained from an infusion pump. J Anal Toxicol 1999;23: 130-133.
7. Sauter K, Kaufman H, Bloomfield S, Cline S. Treatment of high-dose intrathecal morphine overdose case report. J Neurosurg 1994;81: 143-146.
8. Wu C L and Patt R B. Accidental overdose of systemic morphine during intended refill on intrathecal infusion device. Anesth Analges 1992;75: 130-132.
9. Winnie A P, Pappas G D, DasGupta T K, Wang H. Subarachnoid adrenal medullary transplants for terminal cancer pain. Anesthesiology 1993;79: 644-653.
10. Wu H H, Wilcox G L, McLoon S C. Implantation of AtT-20 or genetically modified AtT-20/hENK cells in mouse spinal cord induced antinociception and opioid tolerance. J Neurosci 1994;14: 4806-4814.
11. Eaton M J, Dancausse H R, Santiago D I, Whittemore S R. Lumbar transplants of immortalized serotonergic neurons alleviates chronic neuropathic pain. Pain 1997;72: 59-69.
12. Eaton M J, Plunkett J A, Martinez M A, Lopez T. Transplants of neuronal cells bio-engineered to synthesize GABA alleviate chronic neuropathic pain. Cell Transplant 1999;8: 87-101.
13. Cejas P J, Martinez M, Karmally S, McKillop M. Lumbar transplant of neurons genetically modified to secrete brain-derived neurotrophic factor attenuate allodynia and hyperalgesia after sciatic nerve constriction. Pain 2000;86: 195-210.
14. Eaton M J and Whittemore S R. Autocrine BDNF secretion enhances the survival and serotonergic differentiation of raphe neuronal precursor cells grafted into the adult rat CNS. Exp Neurol 1996;140: 105-114.
15. Andrews P W, Damjanov I, Simon D, Banting G S. Pluripotent embryonal carcinoma clones derived from human teratocarcinoma cell line Tera-2. Lab Invest 1984;50: 147-162.
16. Pleasure S J, Page C, Lee V M Y. Pure, postmitotic, polarized human neurons derived from NTera 2 cells provide a system for expressing exogenous proteins in terminally differentiated neurons. J Neurosci 1992;12: 1802-1815.
17. Borlongan C V, Tajima Y, Trojanowski J Q, Lee V M Y. Transplantation of cryopreserved human embryonal carcinoma-derived (NT2 N cells) promotes functional recovery in ischemic rats. Exp Neurol 1998;149: 310-321.
18. Trojanowski J Q, Kleppner S R, Hartley R S, Miyazono M. Transfectable and transplantable postmitotic human neurons: potential "platform" for gene therapy of nervous system diseases. Exp Neurol 1997;144: 92-97.
19. Kondziolka D, Wechsler L, Goldstein S, Meltzer C. Transplantation of cultured human neuronal cells for patients with stroke. Neurology 2000;55: 565-569.
20. Nelson P T, Kondziolka D, Wechsler L, Goldstein S. Clonal human (hNT) neuron grafts for stroke therapy: neuropathology in a patient 27 months after implantation. Am J Pathol 2002;160: 1201-1206.
21. Eaton M J, Frydel B, Lopez T, Nie X. Generation and initial characterization of conditionally immortalized chromaffin cells. J Cell Biochem 1999;79: 38-57.
22. Cheung W M W, Fu W Y, Hui W S, Ip N Y. Production of human CNS neurons from embryonal carcinoma cells using a cell aggregation method. BioTechniques 1999;26: 946-954.
23. Sarnat H B, Nochlin D, Born D E. Neuronal nuclear antigen (NeuN): a marker of neuronal maturation in early human fetal nervous system. Brain Dev 1998;20: 88-94.
24. Daadi M M, Saporta S; Willing A E, Zigova T. In vitro induction and in vivo expression of bcl-2 in the hNT neurons. Brain Res Bull 2001;56: 147-152.
25. Eaton M J, Staley J K, Globus M Y T, Whittemore S R. Developmental regulation of early serotonergic neuronal differentiation: the role of brain-derived neurotrophic factor and membrane depolarization. Dev Biol 1995;170: 169-182.
26. Bennett D J, Gorassini M, Fouad K, Sanelli L. Spasticity in rats with sacral spinal cord injury. J Neurotrauma 1999; 16: 69-84.
27. Siddall P J, Yezierski R P, Loeser J. Pain following spinal cord injury. clinical features, prevalence, and taxonomy. IASP Newsletter 2000;3: 3-7.
28. Hargreaves K, Dubner R, Brown F, Flores C. A new and sensitive method for measuring thermal nociception in cutaneous hyperalgesia. Pain 1988;32: 77-88.
29. Yezierski R P, Liu S, Ruenes G L, Kajander K J. Excitotoxic spinal cord injury: behavioral and morphological characteristics of a central pain model. Pain 1998;75: 141-155.
30. Abraham K E, McGinty J F, Brewer K L. The role of kainic acid/AMPA and metabotropic glutamate receptors in the regulation of opioid mRNA expression and the onset of pain-related behavior following excitotoxic spinal cord injury. Neurosci 2001;104: 863-874.
31. Abraham K E and Brewer K L. Expression of c-fos mRNA is increased and related to dynorphin mRNA expression following excitotoxic spinal cord injury in the rat. Neurosci Lett 2001;307: 187-191.
32. Plunkett J A, Yu C G, Easton J M, Bethea J R. Effects of interleukin-10 (IL-10) on pain behavior and gene expression following excitotoxic spinal cord injury in the rat. Exp Neurol 2001;168: 144-154.
33. Abraham K E, McGinty J F, Brewer K L. Spinal and supraspinal changes in opioid mRNA expression are related to the onset of pain behaviors following spinal cord injury. Pain 2001;90: 181-190.
34. Abraham K E, Brewer K L, McGinty J F. Opioid peptide messenger RNA expression is increased at spinal and supraspinal levels following excitotoxic spinal cord injury. Neurosci 2000;99: 189-197.
35. Morrow T J, Paulson P E, Brewer K L, Yezierski R P. Chronic, selective forebrain responses to excitotoxic dorsal horn injury. Exp Neurol 2000;161: 220-226.
36. Brewer K L and Yezierski R P. Effects of adrenal medullary transplants on pain-related behaviors following excitotoxic spinal cord injury. Pain 1998;798: 83-92.
37. Schwartz E D, Yezierski R P, Pattany P M, Quencer R M. Diffusion-weighted MR imaging in a rat model of syringomyelia after excitotoxic spinal cord injury. Am J Neuroradiol 1999;20: 1422-1428.
38. Yezierski R P, Santana M, Park S H, Madsen P W. Neuronal degeneration and spinal cavitation following intraspinal injections of quisqualic acid in the rat. J Neurotrauma 1993;10: 445-456.
39. Widerstrom-Noga E G, Felipe-Cuervo E, Broton J G, Duncan R C. Perceived difficulty in dealing with consequences of spinal cord injury. Arch Phys Med Rehabil 1999;80: 580-586.
40. Yezierski R P. Pain following spinal cord injury: the clinical problem and experimental studies. Pain 1996;68: 185-194.
41. Bennett G J and Xie Y-K. A peripheral mononeuropathy in rat that produces disorders of pain sensation like those seen in man. Pain 1988;33: 87-107.
42. Kim S H and Chung J M. An experimental model for peripheral neuropathy produced by segmental spinal nerve ligation in the rat. Pain 1992;50: 355-363.

43. Yezierski R P, Liu S, Ruenes G L, Kajander K J. Behavioral and pathological characteristics of a central pain model following spinal injury. VIIIth World Congress on Pain 1996;
44. Yezierski R P and Park S H. The mechanosensitivity of spinal sensory neurons following intraspinal injections of quisqualic acid in the rat. Neurosci Lett 1998;157: 115-119.
45. Smart D, Hirst R A, Hirota K, Grandy D K, Lambert D G. The effects of recombinant rat mu-opioid receptor activation in CHO cells on phopholipase C, [Ca2+]i and adenyl cyclase. Br J Pharmacol 1997; 120: 1165-1171.

What is claimed is:

1. The cell line deposited with the American Type Culture Collection (ATCC) Manassas, Va. (USA), under Designation No. PTA-7154, or progeny thereof.

2. A method of treating a neurological disease, condition, or disorder, comprising:

transplanting in a subject in need thereof a suitable amount of, the cells of claim 1 in or adjacent to the spinal cord of the subject.

* * * * *